United States Patent
Finch et al.

(10) Patent No.: US 9,458,154 B2
(45) Date of Patent: *Oct. 4, 2016

(54) KINASE INHIBITORS

(75) Inventors: Harry Finch, Parma (IT); Monique Bodil Van Niel, Parma (IT); Chi-Kit Woo, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/363,556

(22) PCT Filed: Dec. 9, 2011

(86) PCT No.: PCT/EP2011/072375
§ 371 (c)(1),
(2), (4) Date: Sep. 11, 2014

(87) PCT Pub. No.: WO2013/083206
PCT Pub. Date: Jun. 13, 2013

(65) Prior Publication Data
US 2015/0057273 A1    Feb. 26, 2015

(51) Int. Cl.
| C07D 471/04 | (2006.01) |
| C07D 403/12 | (2006.01) |
| A61K 9/00 | (2006.01) |
| C07D 401/12 | (2006.01) |

(52) U.S. Cl.
CPC .............. *C07D 471/04* (2013.01); *A61K 9/007* (2013.01); *C07D 401/12* (2013.01); *C07D 403/12* (2013.01)

(58) Field of Classification Search
CPC .................................................. C07D 471/04
See application file for complete search history.

(56) References Cited

U.S. PATENT DOCUMENTS

| 8,835,431 B2* | 9/2014 | Van Niel et al. .......... 514/233.2 |
| 8,907,094 B2* | 12/2014 | Van Niel et al. ............ 546/119 |
| 8,916,708 B2* | 12/2014 | Woo et al. .................... 546/112 |
| 2003/0008868 A1 | 1/2003 | Francesco Cirillo et al. |
| 2009/0012079 A1 | 1/2009 | Lewthwaite et al. |

FOREIGN PATENT DOCUMENTS

| WO | 02 092576 | 11/2002 |
| WO | 2007 091152 | 8/2007 |
| WO | 2011 154738 | 12/2011 |

OTHER PUBLICATIONS

Johnson, A. W. Invitation to Organic Chemistry 1999 Jones and Bartlett: Mississauga, Canada, p. 24.*
US Food and Drug Administration "Development of New Stereoisomeric Drugs" Publication Date: May 1, 1992.*
Aboul-Enein, H. Y. editor, "Separation Techniques in Clinical Chemistry" 2003, Marcel Dekker pp. 158-159.*
International Search Report Issued Sep. 5, 2012 in PCT/EP11/072375 Filed Dec. 9, 2011.
Written Opinion of the International Searching Authority Issued Sep. 5, 2012 in PCT/EP11/072375 Filed Dec. 9, 2011.

* cited by examiner

*Primary Examiner* — David K O'Dell
(74) *Attorney, Agent, or Firm* — Oblon, McClelland, Maier & Neustadt, L.L.P

(57) ABSTRACT

Disclosed are compounds having [1,2,4]triazolo[4,3-a]pyridine groups and pharmaceutically acceptable salts thereof. The compounds are p38 MAPK inhibitors, useful as anti-inflammatory agents in the treatment of, inter alia, diseases of the respiratory tract.

13 Claims, No Drawings

KINASE INHIBITORS

This invention relates to compounds and compositions that are p38 MAPK inhibitors, useful as anti-inflammatory agents in the treatment of, inter alia, diseases of the respiratory tract.

BACKGROUND TO THE INVENTION

Mitogen activated protein kinases (MAPK) constitute a family of proline-directed serine/threonine kinases that activate their substrates by dual phosphorylation. There are four known human isoforms of p38 MAP kinase, p38α, p38β, p38γ and p38δ. The p38 kinases, which are also known as cytokine suppressive anti-inflammatory drug binding proteins (CSBP), stress activated protein kinases (SAPK) and RK, are responsible for phosphorylating (Stein et al., Ann Rep. Med Chem., 1996, 31, 289-298) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (Herlaar E. & Brown Z., Molecular Medicine Today, 1999, 5, 439-447). The products of p38 phosphorylation have been shown to mediate the production of inflammatory cytokines, including tumor necrosis factor alpha (TNF α) and interleukin-(IL-)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (e.g. Dinarello et al., Rev. Infect. Disease, 1984, 6, 51). Excessive or unregulated TNF production (particularly TNFα) has been implicated in mediating or exacerbating a number of diseases, and it is believed that TNF can cause or contribute to the effects of inflammation in general. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (Badger et al., J. Pharm. Exp. Thera., 1996, 279, 1453-1461; Griswold et al, Pharmacol. Comm., 1996, 7, 323-229). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α, IL-1β, IL-6, IL-4, IL-5 and IL-13 (Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Crit. Care Med., 171, 571-578; Escott et al Br. J. Pharmacol., 2000, 131, 173-176; Underwood et al., J. Pharmacol. Exp. Ther. 2000, 293, 281-288). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (Lee et al., Immunopharmacology, 2000, 47, 185-200). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425). It is believed that the compounds of the present invention can be used to treat p38 mediated diseases such as: asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (but non-malignant) conditions, such as hemangiomas, angiofibroma of the nasopharynx, and avascular necrosis of bone, benign and malignant tumors/neoplasia including cancer, leukaemia, lymphoma, systemic lupus erythematosus (SLE), angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV7), human herpesvirus-8 (HHV-8), pseudorabies and rhinotracheitis, among others.

Known P38 kinase inhibitors have been reviewed by G. J. Hanson (Expert Opinions on Therapeutic Patents, 1997, 7, 729-733) J Hynes et al. (Current Topics in Medicinal Chemistry, 2005, 5, 967-985), C. Dominguez et al (Expert Opinions on Therapeutics Patents, 2005, 15, 801-816) and L. H. Pettus & R. P. Wurtz (Current Topics in Medicinal Chemistry, 2008, 8, 1452-1467). P38 kinase inhibitors containing a triazolopyridine motif are known in the art, for example WO07/091152, WO04/072072, WO06/018727.

BRIEF DESCRIPTION OF THE INVENTION

The compounds of the present invention are inhibitors of p38 mitogen activated protein kinase ("p38 MAPK", "p38 kinase" or "p38"), including p38 kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease ("COPD") and asthma. They are therefore particularly suited for pulmonary delivery, by inhalation by nose or mouth.

SUMMARY OF THE INVENTION

Our copending international patent application No. PCT/GB2011/051076 is concerned, inter alia, with compounds of formula (I) that are p38 MAPK inhibitors, useful as anti-inflammatory agents in the treatment of, inter alia, diseases of the respiratory tract:

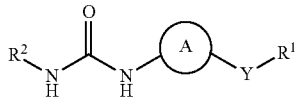
(I)

wherein:
$R^1$ is a radical of formula (IA) or (IB) or (IC):

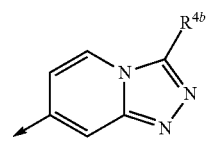
(IA)

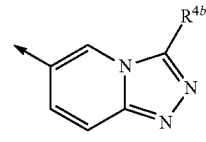
(IB)

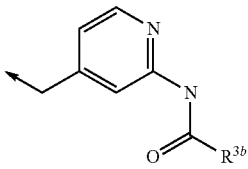
(IC)

wherein
$R^{4b}$ is $C_1$-$C_6$ alkyl, $C_3$-$C_6$ cycloalkyl, optionally substituted phenyl, optionally substituted 5- or 6-membered monocyclic heteroaryl or a radical of formula (IIa) or (IIb)

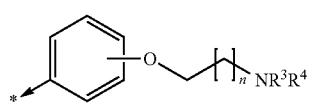
(IIa)

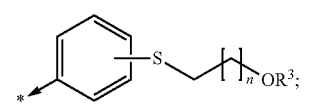
(IIb)

wherein n is 1 or 2; and $R^3$ and $R^4$ are independently H or $C_1$-$C_6$ alkyl, or $R^3$ and $R^4$ taken together with the nitrogen to which they are attached form a 6-membered heterocyclic ring optionally containing a further heteroatom selected from N and O;

$R^{3b}$ is optionally substituted $C_1$-$C_6$ alkyl; —$NH_2$; mono- or di-($C_1$-$C_6$) alkylamino; mono- or di-($C_1$-$C_3$) alkyl-X—($C_1$-$C_3$)alkylamino wherein X is O, S or NH; N-morpholino; N-piperidinyl, N-piperazinyl or N—($C_1$-$C_3$)alkylpiperazin-1-yl;

Y is —O— or —S(O)$_p$— wherein p is 0, 1 or 2;

A is an optionally substituted cycloalkylene radical having 5, 6 or 7 ring atoms fused to a phenyl ring;

$R^2$ is a radical of formula (IIIa), (IIIb), (IIIc), (IIId) or (IIIe):

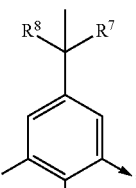
(IIIa)

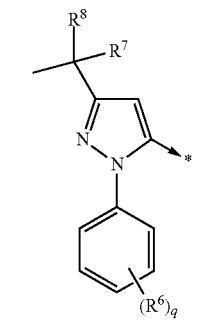
(IIIb)

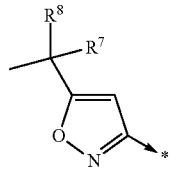
(IIIc)

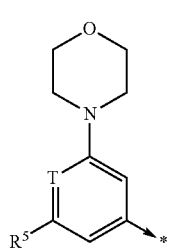
(IIId)

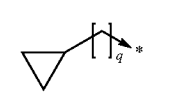
(IIIe)

wherein
q is 0, 1, 2 or 3;
T is —N= or —CH=;
$R^5$ is H or F;
$R^7$ is —$CH_3$; —$C_2H_5$; —$CH_2OH$, —$CH_2SCH_3$; —$SCH_3$ or —$SC_2H_5$;
$R^8$ is —$CH_3$ or —$C_2H_5$; and each occurrence of $R^6$ is independently H, $C_1$-$C_6$ alkyl, hydroxy or halo; or a single occurrence of $R^6$ is a radical of formula (IVa), (IVb) or (IVc)

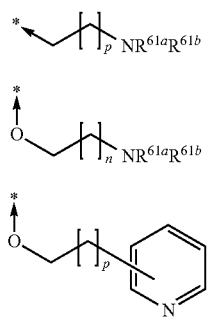

while any other occurrence of $R^6$ is independently H, $C_1$-$C_6$ alkyl, hydroxyl or halo;

wherein in formulae (IVa), (IVb) and (IVc) n and p are as defined above;

and wherein in $R^6$ $R^{61a}$ and $R^{61b}$ are H, alkyl, or $R^{61a}$ and $R^{61b}$ may be joined together with the nitrogen to which they are attached to form a 4-7 membered heterocyclic ring optionally containing a further heteroatom selected from N and O, such as a piperidine, piperazine or morpholine ring.

The present invention relates to compounds which are p38 MAPK inhibitors falling within the scope of Formula (I) of No. PCT/GB2011/051076, but not specifically disclosed therein.

DESCRIPTION OF THE INVENTION

According to the present invention, there is provided a compound selected from the group consisting of:

1-(5-tert-Butyl-2-phenyl-2H-pyrazol-3-yl)-3-[4-(3-isopropyl-[1,2,4]triazolo[4,3-a]pyridin-6-yloxy)-1,2,3,4-tetrahydro-naphthalen-1-yl]-urea;

1-Cyclopropyl-3-[4-(3-isopropyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[3-(3-isopropyl-[1,2,4]triazolo[4,3-a]pyridin-6-ylsulfanyl)-indan-1-yl]-urea;

1-(5-tert-Butyl-2-p-tolyl-2H-pyrazol-3-yl)-3-[4-{3-[3-(2-morpholin-4-yl-ethoxy)-phenyl]-[1,2,4]triazolo[4,3-a]pyridin-6-yloxy}-1,2,3,4-tetrahydro-naphthalen-1-yl)-urea;

1-(5-tert-Butyl-2-p-tolyl-2H-pyrazol-3-yl)-3-[4-(3-isopropyl-[1,2,4]triazolo[4,3-a]pyridin-7-yloxy)-1,2,3,4-tetrahydro-naphthalen-1-yl]-urea;

1-{5-tert-Butyl-2-[3-(2-morpholin-4-yl-ethoxy)-phenyl]-2H-pyrazol-3-yl}-3-[4-(3-isopropyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-{4-(3-(2-hydroxy-phenyl)-[1,2,4]triazolo[4,3-a]pyridin-6-yloxy)-1,2,3,4-tetrahydro-naphthalen-1-yl}-urea;

1-(5-tert-Butyl-isoxazol-3-yl)-3-[3-(3-isopropyl-[1,2,4]triazolo[4,3-a]pyridin-6-yloxy)-indan-1-yl]-urea;

N-(4-{4-[3-(5-tert-Butyl-2-p-tolyl-2H-pyrazol-3-yl)-ureido]-1,2,3,4-tetrahydro-naphthalen-1-yloxymethyl}-pyridin-2-yl)-2-methoxy-acetamide;

1-(5-tert-Butyl-2-p-tolyl-2H-pyrazol-3-yl)-3-{4-[3-(2-hydroxy-ethylsulfanyl)-phenyl]-[1,2,4]triazolo[4,3-a]pyridin-6-yloxy)-1,2,3,4-tetrahydro-naphthalen-1-yl-urea;

1-{5-tert-Butyl-2-[3-(2-dimethylamino-ethoxy)-phenyl]-2H-pyrazol-3-yl}-3-[4-(3-isopropyl-[1,2,4]triazolo[4,3-a]pyridin-6-yloxy)-1,2,3,4-tetrahydro-naphthalen-1-yl]-urea;

1-[5-tert-Butyl-2-(4-hydroxy-phenyl)-2H-pyrazol-3-yl]-3-[4-(3-isopropyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[4-(3-tert-butyl-[1,2,4]triazolo[4,3-a]pyridin-6-yloxy)-1,2,3,4-tetrahydro-naphthalen-1-yl]-urea;

1-(5-tert-Butyl-isoxazol-3-yl)-3-[4-(3-isopropyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[4-(3-cyclopentyl-[1,2,4]triazolo[4,3-a]pyridin-6-yloxy)-1,2,3,4-tetrahydro-naphthalen-1-yl]-urea;

1-[5-tert-Butyl-2-(3-morpholin-4-ylmethyl-phenyl)-2H-pyrazol-3-yl]-3-[4-(3-isopropyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl-3-{4-(3-(2,6-dichloro-phenyl)-[1,2,4]triazolo[4,3-a]pyridin-6-yloxy)-1,2,3,4-tetrahydro-naphthalen-1-yl}-urea;

1-(5-tert-Butyl-2-p-tolyl-2H-pyrazol-3-yl)-3-[4-(3-cyclopropyl-[1,2,4]triazolo[4,3-a]pyridin-6-yloxy)-1,2,3,4-tetrahydro-naphthalen-1-yl}-urea;

1-(5-tert-Butyl-2-p-tolyl-2H-pyrazol-3-yl)-3-[4-(3-pyridin-2-yl-[1,2,4]triazolo[4,3-a]pyridin-6-yloxy)-1,2,3,4-tetrahydro-naphthalen-1-yl}-urea;

1-(5-tert-Butyl-2-p-tolyl-2H-pyrazol-3-yl-3-{4-(3-(2-chloro-phenyl)-[1,2,4]triazolo[4,3-a]pyridin-6-yloxy)-1,2,3,4-tetrahydro-naphthalen-1-yl}-urea;

1-{4-[3-(2-Benzyloxy-phenyl)-[1,2,4]triazolo[4,3-a]pyridin-6-yloxy)-1,2,3,4-tetrahydro-naphthalen-1-yl}-3-(5-tert-butyl-2-p-tolyl-2H-pyrazol-3-yl)-urea;

1-[5-tert-Butyl-2-(3-chloro-4-hydroxy-phenyl)-2H-pyrazol-3-yl]-3-[4-(3-isopropyl-[1,2,4]triazolo[4,3-a]pyridin-6-yloxy)-1,2,3,4-tetrahydro-naphthalen-1-yl]urea;

1-(5-tert-Butyl-2-p-tolyl-2H-pyrazol-3-yl)-3-[4-(3-cyclohexyl-[1,2,4]triazolo[4,3-a]pyridin-6-yloxy)-1,2,3,4-tetrahydro-naphthalen-1-yl]-urea;

1-[5-tert-Butyl-2-(4-chloro-3-hydroxy-phenyl)-2H-pyrazol-3-yl]-3-[4-(3-isopropyl-[1,2,4]triazolo[4,3-a]pyridin-6-yloxy)-1,2,3,4-tetrahydro-naphthalen-1-yl]-urea;

N-(5-tert-Butyl-3-{3-[4-(3-isopropyl-[1,2,4]triazolo[4,3-a]pyridin-6-yloxy)-1,2,3,4-tetrahydro-naphthalen-1-yl]-ureido}-2-methoxy-phenyl)-methane sulfonamide;

1-(3-Fluoro-5-morpholin-4-yl-phenyl)-3-[4-(3-isopropyl-[1,2,4]triazolo[4,3-a]pyridin-6-yloxy)-1,2,3,4-tetrahydro-naphthalen-1-yl]-urea;

1-{5-tert-Butyl-2-(4-fluoro-3-morpholin-4-ylmethyl-phenyl)-2H-pyrazol-3-yl}-3-[4-(3-isopropyl-[1,2,4]triazolo[4,3-a]pyridin-6-yloxy)-1,2,3,4-tetrahydro-naphthalen-1-yl]-urea;

1-[5-tert-Butyl-2-(3-chloro-4-hydroxy-phenyl)-2H-pyrazol-3-yl]-3-(4-{3-[2-(2-hydroxy-ethylsulfanyl)-phenyl]-[1,2,4]triazolo[4,3-a]pyridin-6-yloxy}-1,2,3,4-tetrahydro-naphthalen-1-yl)-urea;

1-[5-tert-Butyl-2-(3-chloro-4-hydroxy-phenyl)-2H-pyrazol-3-yl]-3-(4-{3-[2-(2-hydroxy-ethylsulfanyl)-phenyl]-[1,2,4]triazolo[4,3-a]pyridin-6-yloxy}-1,2,3,4-tetrahydro-naphthalen-1-yl)-urea;

1-(5-tert-Butyl-2-p-tolyl-2H-pyrazol-3-yl)-3-{(4-[3-(2-pyrrolidin-1-yl-pyridin-4-yl)-[1,2,4]triazolo[4,3-a]pyridin-6-yloxy]-1,2,3,4-tetrahydro-naphthalen-1-yl}-urea;

And pharmaceutically acceptable salts thereof.

In particular, the present invention provides a compound selected from the group consisting of those of listed in the Table herebelow, or a pharmaceutically acceptable salt thereof:

| Compound Name | Example number |
|---|---|
| 1-(5-tert-Butyl-2-phenyl-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea | 1 |
| 1-Cyclopropyl-3-[(1S,4S)-4-(3-isopropyl-[1,2,4]triazolo[4,3-a]pyridin-6-yloxy)-1,2,3,4-tetrahydro-naphthalen-1-yl]-urea | 2 |
| (±)-trans-1-(5-tert-Butyl-2-p-tolyl-2H-pyrazol-3-yl)-3-[3-(3-isopropyl-[1,2,4]triazolo[4,3-a]pyridin-6-ylsulfanyl)-indan-1-yl]-urea | 3 |
| 1-(5-tert-Butyl-2-p-tolyl-2H-pyrazol-3-yl)-3-[(1S,4R)-4-{3-[3-(2-morpholin-4-yl-ethoxy)-phenyl]-[1,2,4]triazolo[4,3-a]pyridin-6-yloxy}-1,2,3,4-tetrahydro-naphthalen-1-yl)-urea | 4 |
| 1-(5-tert-Butyl-2-p-tolyl-2H-pyrazol-3-yl)-3-[(1S,4R)-4-(3-isopropyl-[1,2,4]triazolo[4,3-a]pyridin-7-yloxy)-1,2,3,4-tetrahydro-naphthalen-1-yl]-urea | 5 |
| 1-{5-tert-Butyl-2-[3-(2-morpholin-4-yl-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea | 6 |
| 1-(5-tert-Butyl-2-p-tolyl-2H-pyrazol-3-yl)-3-{(1S,4R)-4-[3-(2-hydroxy-phenyl)-[1,2,4]triazolo[4,3-a]pyridin-6-yloxy)-1,2,3,4-tetrahydro-naphthalen-1-yl}-urea | 7 |
| 1-(5-tert-Butyl-isoxazol-3-yl)-3-[(1S,3S)-3-(3-isopropyl-[1,2,4]triazolo[4,3-a]pyridin-6-yloxy)-indan-1-yl]-urea | 8 |
| N-(4-{(1R,4S)-4-[3-(5-tert-Butyl-2-p-tolyl-2H-pyrazol-3-yl)-ureido]-1,2,3,4-tetrahydro-naphthalen-1-yloxymethyl}-pyridin-2-yl)-2-methoxy-acetamide | 9 |
| 1-(5-tert-Butyl-2-p-tolyl-2H-pyrazol-3-yl)-3-{(1S,4R)-4-[3-(2-hydroxy-ethylsulfanyl)-phenyl]-[1,2,4]triazolo[4,3-a]pyridin-6-yloxy)-1,2,3,4-tetrahydro-naphthalen-1-yl-urea | 10 |
| 1-{5-tert-Butyl-2-[3-(2-dimethylamino-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea | 11 |
| 1-[5-tert-Butyl-2-(3-chloro-4-hydroxy-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea | 12 |
| 1-Cyclopropyl-3-[(1S,4R)-4-(3-isopropyl-[1,2,4]triazolo[4,3-a]pyridin-6-yloxy)-1,2,3,4-tetrahydro-naphthalen-1-yl]-urea | 13 |
| 1-(5-tert-Butyl-2-(4-chloro-3-hydroxyphenyl)-2H-pyrazol-3-yl)-3-[(1S,4R)-4-(3-isopropyl-[1,2,4]triazolo[4,3-a]pyridin-6-yloxy)-1,2,3,4-tetrahydronaphthalen-1-yl]-urea | 14 |
| 1[5-tert-Butyl-2-(4-hydroxy-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea | 15 |
| 1-(5-tert-Butyl-2-p-tolyl-2H-pyrazol-3-yl)-3-[(1S,4R)-4-(3-tert-butyl-[1,2,4]triazolo[4,3-a]pyridin-6-yloxy)-1,2,3,4-tetrahydro-naphthalen-1-yl]-urea | 16 |
| 1-(5-tert-Butyl-isoxazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea | 17 |
| 1-(5-tert-Butyl-2-p-tolyl-2H-pyrazol-3-yl)-3-[(1S,4R)-4-(3-cyclopentyl-[1,2,4]triazolo[4,3-a]pyridin-6-yloxy)-1,2,3,4-tetrahydro-naphthalen-1-yl]-urea | 18 |
| 1-[5-tert-Butyl-2-(3-morpholin-4-ylmethyl-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea | 19 |
| 1-(5-tert-Butyl-2-p-tolyl-2H-pyrazol-3-yl)-3-{(1S,4R)-4-(3-(2,6-dichloro-phenyl)-[1,2,4]triazolo[4,3-a]pyridin-6-yloxy)-1,2,3,4-tetrahydro-naphthalen-1-yl}-urea | 20 |
| 1-(5-tert-Butyl-2-p-tolyl-2H-pyrazol-3-yl)-3-[(1S,4R)-4-(3-cyclopropyl-[1,2,4]triazolo[4,3-a]pyridin-6-yloxy)-1,2,3,4-tetrahydro-naphthalen-1-yl}-urea | 21 |
| 1-(5-tert-Butyl-2-p-tolyl-2H-pyrazol-3-yl)-3-[(1S,4R)-4-(3-pyridin-2-yl-[1,2,4]triazolo[4,3-a]pyridin-6-yloxy)-1,2,3,4-tetrahydro-naphthalen-1-yl]-urea | 22 |
| 1-(5-tert-Butyl-2-p-tolyl-2H-pyrazol-3-yl-3-{(1S,4R)-4-(3-(2-chloro-phenyl)-[1,2,4]triazolo[4,3-a]pyridin-6-yloxy)-1,2,3,4-tetrahydro-naphthalen-1-yl}-urea | 23 |
| 1-{(1S,4R)-4-[3-(2-Benzyloxy-phenyl)-[1,2,4]triazolo[4,3-a]pyridin-6-yloxy)-1,2,3,4-tetrahydro-naphthalen-1-yl}-3-(5-tert-butyl-2-p-tolyl-2H-pyrazol-3-yl)-urea | 24 |
| 1-[5-tert-Butyl-2-(3-chloro-4-hydroxy-phenyl)-2H-pyrazol-3-yl]-3-[(1S,4S)-4-(3-isopropyl-[1,2,4]triazolo[4,3-a]pyridin-6-yloxy)-1,2,3,4-tetrahydro-naphthalen-1-yl]-urea | 25 |
| 1-(5-tert-Butyl-2-p-tolyl-2H-pyrazol-3-yl)-3-[(1S,4R)-4-(3-cyclohexyl-[1,2,4]triazolo[4,3-a]pyridin-6-yloxy)-1,2,3,4-tetrahydro-naphthalen-1-yl]-urea | 26 |
| 1-[5-tert-Butyl-2-(4-chloro-3-hydroxy-phenyl)-2H-pyrazol-3-yl]-3-[(1S,4S)-4-(3-isopropyl-[1,2,4]triazolo[4,3-a]pyridin-6-yloxy)-1,2,3,4-tetrahydro-naphthalen-1-yl]-urea | 27 |
| N-(5-tert-Butyl-3-{3-[(1S,4R)-4-(3-isopropyl-[1,2,4]triazolo[4,3-a]pyridin-6-yloxy)-1,2,3,4-tetrahydro-naphthalen-1-yl]-ureido}-2-methoxy-phenyl)-methanesulfonamide | 28 |
| 1-(3-Fluoro-5-morpholin-4-yl-phenyl)-3-[(1S,4R)-4-(3-isopropyl-[1,2,4]triazolo[4,3-a]pyridin-6-yloxy)-1,2,3,4-tetrahydro-naphthalen-1-yl]urea | 29 |
| 1-(3-Fluoro-5-morpholin-4-yl-phenyl)-3-[(1S,4S)-4-(3-isopropyl-[1,2,4]triazolo[4,3-a]pyridin-6-yloxy)-1,2,3,4-tetrahydro-naphthalen-1-yl]urea | 30 |
| 1-{5-tert-Butyl-2-(4-fluoro-3-morpholin-4-ylmethyl-phenyl)-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea | 31 |
| 1-[5-tert-Butyl-2-(3-chloro-4-hydroxy-phenyl)-2H-pyrazol-3-yl]-3-((1S,4R)-4-{3-[2-(2-hydroxy-ethylsulfanyl)-phenyl]-[1,2,4]triazolo[4,3-a]pyridin-6-yloxy}-1,2,3,4-tetrahydro-naphthalen-1-yl)-urea | 32 |
| 1-[5-tert-Butyl-2-(3-chloro-4-hydroxy-phenyl)-2H-pyrazol-3-yl]-3-((1S,4S)-4-{3-[2-(2-hydroxy-ethylsulfanyl)-phenyl]-[1,2,4]triazolo[4,3-a]pyridin-6-yloxy}-1,2,3,4-tetrahydro-naphthalen-1-yl)-urea | 33 |
| 1-(5-tert-Butyl-2-p-tolyl-2H-pyrazol-3-yl)-3-{(1S,4R)-4-[3-(2-pyrrolidin-1-yl-pyridin-4-yl)-[1,2,4]triazolo[4,3-a]pyridin-6-yloxy]-1,2,3,4-tetrahydro-naphthalen-1-yl}-urea | 34 |

In another aspect, the invention includes pharmaceutical compositions comprising a compound of the invention, together with one or more pharmaceutically acceptable carriers and/or excipients. Particularly preferred are compositions adapted for inhalation for pulmonary administration.

In another aspect, the invention includes the use of a compound of the invention for the treatment of diseases or conditions which benefit from inhibition of p38 MAP kinase activity. The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, asthma, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, chronic inflammatory diseases including cystic fibrosis, bronchiectasis and pulmonary fibrosis (Idiopathic). Efficacy is anticipated when p38 kinase inhibitors are administered either locally to the lung (for example by inhalation and intranasal delivery) or via systemic routes (for example, oral, intravenous and subcutaneous delivery).

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis).

As used herein the term "salt" includes base addition, acid addition and ammonium salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds of the invention which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, trifluoroacetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds of the invention which have a basic nitrogen can also form quaternary ammonium salts with a pharmaceutically acceptable counter-ion such as ammonium, chloride, bromide, acetate, formate, p-toluenesulfonate, succinate, hemi-succinate, naphthalene-bis sulfonate, methanesulfonate, trifluoroacetate, xinafoate, and the like. For a review on salts, see *Handbook of Pharmaceutical Salts: Properties, Selection, and Use* by Stahl and Wermuth (Wiley-VCH, Weinheim, Germany, 2002).

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in several polymorphic forms and may be obtained in different crystal habits.

The compounds may also be administered in the form of prodrugs thereof. Thus certain derivatives of the compounds which may be active in their own right or may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, 3rd Edition, 2002, Taylor and Francis).

Prodrugs in accordance with the invention can, for example, be produced by replacing appropriate functionalities present in the compounds of the invention with certain moieties known to those skilled in the art as 'pro-moieties' as described, for example, in *Design of Prodrugs* by H. Bundgaard (Elsevier, 1985).

EMBODIMENTS OF THE INVENTION

In one embodiment, the compounds of invention are compounds of formula (Ia) or pharmaceutically acceptable salts thereof:

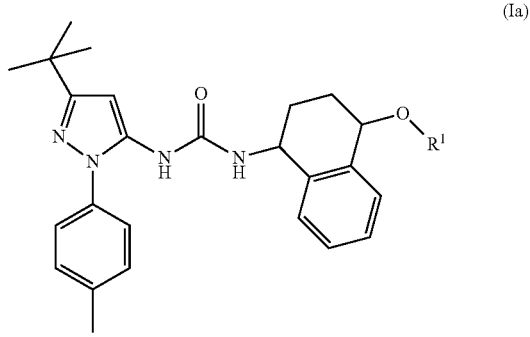

(Ia)

wherein the group R¹ is selected in the group consisting of:
3-[3-(2-morpholin-4-yl-ethoxy)-phenyl]-[1,2,4]triazolo[4,3-a]pyridin-6-yl;
(3-isopropyl-[1,2,4]triazolo[4,3-a]pyridin-7-yl;
3-(2-hydroxy-phenyl)-[1,2,4]triazolo[4,3-a]pyridin-6-yl;
{2-[(methoxyacetyl)amino]pyridin-4-yl}methyl;
3-[3-(2-hydroxy-ethylsulfanyl)-phenyl]-[1,2,4]triazolo[4,3-a]pyridin-6-yl;
3-tert-butyl-[1,2,4]triazolo[4,3-a]pyridin-6-yl;
3-cyclopentyl-[1,2,4]triazolo[4,3-a]pyridin-6-yl;
3-(2,6-dichloro-phenyl)-[1,2,4]triazolo[4,3-a]pyridin-6-yl;
3-cyclopropyl-[1,2,4]triazolo[4,3-a]pyridin-6-yl;
3-pyridin-2-yl-[1,2,4]triazolo[4,3-a]pyridin-6-yl;
3-(2-chloro-phenyl)-[1,2,4]triazolo[4,3-a]pyridin-6-yl;
3-(2-Benzyloxy-phenyl)-[1,2,4]triazolo[4,3-a]pyridin-6-yl;
3-cyclohexyl-[1,2,4]triazolo[4,3-a]pyridin-6-yl;
3-(2-pyrrolidin-1-yl-pyridin-4-yl)-[1,2,4]triazolo[4,3-a]pyridin-6-yl.

In one embodiment, compound of formula (Ia1) are provided, which are compounds of formula (Ia) as above defined where carbon stereogenic center identified with number (1), possess the absolute configuration herebelow represented:

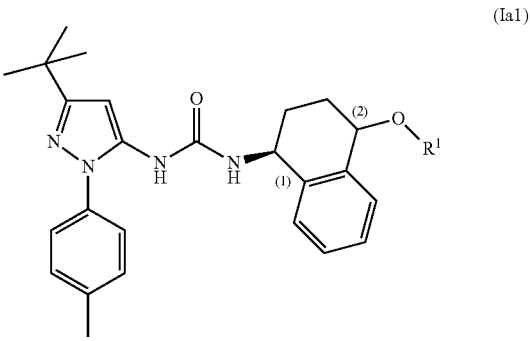

(Ia1)

In a preferred embodiment, compound of formula (Ia2) are provided, which are compounds of formula (Ia) as above defined where carbon stereogenic centers identified with number (1) and (2), possess the absolute configuration herebelow represented:

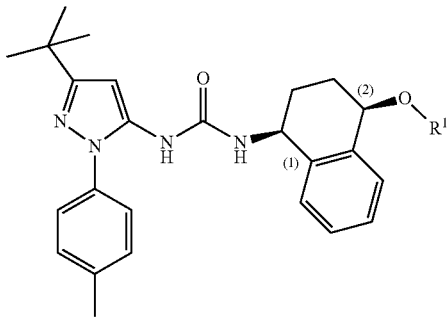

(Ia2)

In another embodiment, the compounds of invention are compounds of formula (Ib) or pharmaceutically acceptable salts thereof:

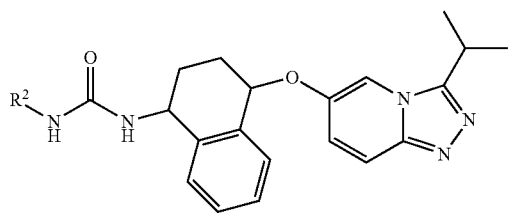

(Ib)

wherein the group R² is selected in the group consisting of:
5-tert-Butyl-2-phenyl-2H-pyrazol-3-yl;
Cyclopropyl;
5-tert-Butyl-2-[3-(2-morpholin-4-yl-ethoxy)-phenyl]-2H-pyrazol-3-yl;
5-tert-Butyl-2-[3-(2-dimethylamino-ethoxy)-phenyl]-2H-pyrazol-3-yl;
5-tert-Butyl-2-(3-chloro-4-hydroxy-phenyl)-2H-pyrazol-3-yl;
5-tert-Butyl-2-(4-chloro-3-hydroxyphenyl)-2H-pyrazol-3-yl;
5-tert-Butyl-2-(4-hydroxy-phenyl)-2H-pyrazol-3-yl;
5-tert-Butyl-isoxazol-3-yl;
5-tert-Butyl-2-(3-morpholin-4-ylmethyl-phenyl)-2H-pyrazol-3-yl;
5-tert-Butyl-3-methanesulfonylamino-2-methoxy-phenyl;
3-Fluoro-5-morpholin-4-yl-phenyl;
5-tert-Butyl-2-(4-fluoro-3-morpholin-4-ylmethyl-phenyl)-2H-pyrazol-3-yl;

In one embodiment, compound of formula (Ib1) are provided, which are compounds of formula (Ib) as above defined where carbon stereogenic center identified with number (1), possess the absolute configuration herebelow represented:

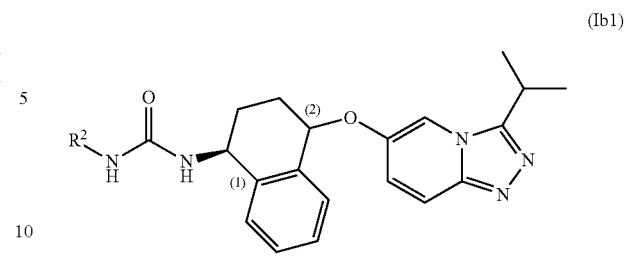

(Ib1)

In a preferred embodiment, compound of formula (Ib2) are provided, which are compounds of formula (Ib) as above defined where carbon stereogenic centers identified with number (1) and (2), possess the absolute configuration herebelow represented:

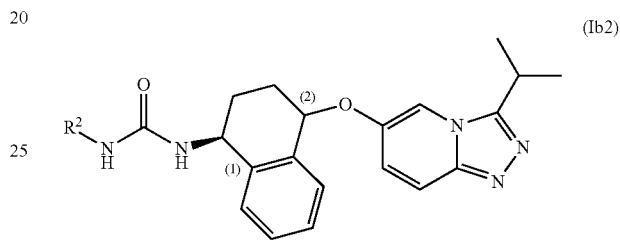

(Ib2)

In a further embodiment, compound of formula (Ib3) are provided, which are compounds of formula (Ib3) as above defined where carbon stereogenic centers identified with number (1) and (2), possess the absolute configuration herebelow represented:

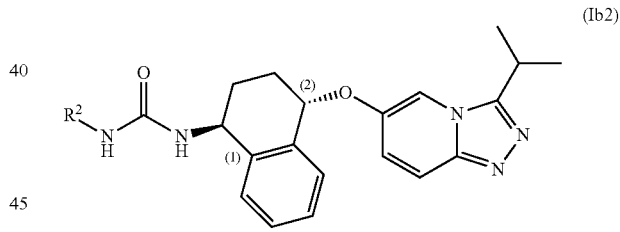

(Ib2)

Utility

As mentioned above the compounds of the invention are p38MAPK inhibitors, and thus may have utility for the treatment of diseases or conditions which benefit from inhibition of the p38 enzyme. Such diseases and conditions are known from the literature and several have been mentioned above. However, the compounds are generally of use as anti-inflammatory agents, particularly for use in the treatment of respiratory disease. In particular, the compounds may be used in the treatment of chronic obstructive pulmonary disease (COPD), chronic bronchitis, lung fibrosis, pneumonia, acute respiratory distress syndrome (ARDS), pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

The present invention provides the use of the compounds of the invention for the prevention and/or treatment of any disease or condition which benefit from inhibition of the p38 enzyme.

In a further aspect the present invention provides the use of compounds of the invention for the preparation of a medicament for the prevention and/or treatment of any disease or condition which benefit from inhibition of the p38 enzyme.

Moreover the present invention provides a method for prevention and/or treatment of any disease which benefit from inhibition of the p38 enzyme, said method comprises administering to a patient in need of such treatment a therapeutically effective amount of a compound of the invention.

Compositions

As mentioned above, the compounds with which the invention is concerned are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases. For the purpose of the invention, inhaled administration is preferred.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

However, for treatment of an inflammatory disease of the respiratory tract, compounds of the invention may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 µm.

In the case of an aerosol-based formulation, an example is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321). Additionally, compounds of the invention may be delivered in multi-chamber devices thus allowing for delivery of combination agents.

Combinations

Other compounds may be combined with compounds with which the invention is concerned for the prevention and treatment of inflammatory diseases, in particular respiratory diseases. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: (1) corticosteroids, such as fluticasone propionate, fluticasone furoate, mometasone furoate, beclometasone dipropionate, ciclesonide, budesonide, GSK 685698, GSK 870086, QAE 397, QMF 149, TPI-1020; (2) β2-adrenoreceptor agonists such as salbutamol, albuterol, terbutaline, fenoterol, and long acting β2-adrenoreceptor agonists such as salmeterol, indacaterol, formoterol (including formoterol fumarate), arformoterol, carmoterol, GSK 642444, GSK 159797, GSK 159802, GSK 597501, GSK 678007, AZD3199; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028; (5) dual pharmacology M3-anticholinergic/β2-adrenoreceptor agonists such as GSK961081; (6) leukotriene modulators, for example leukotriene antagonists such as montelukast, zafirulast or pranlukast or leukotriene biosynthesis inhibitors such as Zileuton or BAY-1005, or LTB4 antagonists such as Amelubant, or FLAP inhibitors such as GSK 2190914, AM-103; (7) phosphodiesterase-IV (PDE-IV) inhibitors (oral or inhaled), such as roflumilast, cilomilast, Oglemilast, ONO-6126, Tetomilast, Tofimilast, UK 500,001, GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723; (9) antitussive agents, such as codeine or dextramorphan; (10) a mucolytic, for example N acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonoclease I (dornase-alfa and rhDNase) or helicidin; (13) antibiotics, for example azithromycin, tobramycin and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO97/03094 and WO97/02289; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO2005/026124, WO2003/053930 and WO06/082412; (20) A2b antagonists such as those described in WO2002/42298; (21) modulators of chemokine receptor function, for example antagonists of CCR3 and CCR8; (22) compounds which modulate the action of other prostanoid receptors, for example a thromboxane $A_2$ antagonist; DPI antagonists such as MK-0524, CRTH2 antagonists such as ODC9101 and AZD1981 and mixed DP1/CRTH2 antagonists such as AMG 009; (23) PPAR agonists including PPAR alpha agonists (such as fenofibrate), PPAR delta agonists, PPAR gamma agonists such as Pioglitazone, Rosiglitazone and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) A2a agonists such as those described in EP1052264 and EP1241176; (26) CXCR2 or IL-8 antagonists such as SCH 527123 or GSK 656933; (27) IL-R signalling modulators such as kineret and ACZ 885; (28) MCP-1 antagonists such as ABN-912.

The invention is also directed to a kit comprising the pharmaceutical compositions of compounds of the invention alone or in combination with or in admixture with one or more pharmaceutically acceptable carriers and/or excipients and a device which may be a single- or multi-dose dry powder inhaler, a metered dose inhaler or a nebulizer.

General Experimental Details

Abbreviations used in the experimental section: AcOH=acetic acid; aq.=aqueous; DCM=dichloromethane; DIAD=Diisopropyl azodicarboxylate; DIPEA=diisopropylethylamine; DMAP=N,N-dimethylaminopyridine; DMF=N,N-dimethylformamide; DMSO=dimethyl sulfoxide; EDC=1-ethyl-3-(3'-dimethylaminopropyl)carbodiimide Hydrochloride; EtOAc=ethyl acetate; EtOH=ethanol; $Et_2O$=diethyl ether; $Et_3N$=triethylamine; $EtNiPr_2$=diisopropylethylamine; FCC=flash column chromatography; h=hour; HATU=2-(7-aza-1H-benzotriazole-1-yl)-1,1,3,3-tetramethyluronium hexafluorophosphate; HOBt=1-hydroxy-benzotriazole; HPLC=high performance liquid chromatography; IMS=Industrial Methylated Spirits; LCMS=liquid chromatography mass spectrometry; NaOH=sodium hydroxide; MeCN=acetonitrile; MeOH=methanol; min(s)=minutes; $NH_3$=ammonia; NMR=nuclear magnetic resonance; RT=room temperature; Rt=retention time; sat.=saturated; SCX-2=strong cation exchange chromatography; TFA=trifluoroacetic acid; THF=Tetrahydrofuran; $H_2O$=water; IMS=industrial methylated spirit; X-Select=Waters X-select HPLC column.

In the procedures that follow, after each starting material, reference to a compound number is sometimes provided. This is provided merely for assistance to the skilled chemist. The starting material may not necessarily have been prepared from the batch referred to.

When reference is made to the use of a “similar” or “analogous” procedure, as will be appreciated by those skilled in the art, such a procedure may involve minor variations, for example reaction temperature, reagent/solvent amount, reaction time, work-up conditions or chromatographic purification conditions.

The nomenclature of structures was assigned using Autonom 2000 Name software from MDL Inc. When the nomenclature of structures could not be assigned using Autonom, ACD/Name software utility part of the ACD/Labs Release 12.00 Product Version 12.5 (Build 45133, 16 Dec. 2010) was used. Stereochemical assignments of compounds are based on NMR comparisons with data reported in WO2008/043019 for key intermediates. All reactions were carried out under anhydrous conditions and an atmosphere of nitrogen or argon unless specified otherwise. Unless otherwise stated all transformations were carried at ambient temperature (room temperature).

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane ($\delta$=0 ppm). J values are given in Hz through-out. NMR spectra were assigned using DataChord Spectrum Analyst Version 4.0.b21 or SpinWorks version 3.

Where products were purified by flash column chromatography, 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash® Companion purification system or use of the Biotage SP1 purification system. All solvents and commercial reagents were used as received.

Compounds purified by preparative HPLC were purified using a C18-reverse-phase column (100×22.5 mm i.d Genesis column with 7 μm particle size), or a Phenyl-Hexyl column (250×21.2 mm i.d. Gemini column with 5 μm particle size), UV detection between 220-254 nm, flow 5-20 mL/min), eluting with gradients from 100-0 to 0-100% water/acetonitrile (containing 0.1% TFA or 0.1% formic acid) or water/MeOH (containing 0.1% TFA or 0.1% formic acid), unless otherwise indicated. Fractions containing the required product (identified by LCMS analysis) were pooled, the organic solvent removed by evaporation, and the remaining aqueous residue lyophilised, to give the final product. Products purified by preparative HPLC were isolated as free base, formate or TFA salts, unless otherwise stated.

The Liquid Chromatography Mass Spectroscopy (LCMS) and HPLC systems used are:

Method 1

Waters Platform LC Quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient-Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line HP1100 DAD detector). MS ionization method—Electrospray (positive and negative ion).

Method 2

Waters ZMD quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient-Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line Waters 996 DAD detector). MS ionization method—Electrospray (positive and negative ion).

Method 3

Waters ZMD quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient-Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line HP1100 DAD detector). MS ionization method—Electrospray (positive and negative ion).

Method 4

VG Platform II quadrupole spectrometer with a C18-reverse-phase column (30×4.6 mm Phenomenex Luna 3 μm particle size, elution with A: water+0.1% formic acid; B: acetonitrile+0.1% formic acid. Gradient:

| Gradient-Time | flow mL/min | % A | % B |
| --- | --- | --- | --- |
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (200 μl/min split to the ESI source with inline HP1050 DAD detector). MS ionization method—Electrospray (positive and negative ion).

Method 5

Waters micromass ZQ2000 quadrupole mass spectrometer with an Acquity BEH C18 1.7 um 100×2.1 mm, Acquity BEH Shield RP18 1.7 um 100×2.1 mm or Acquity HSST3 1.8 um 100×2.1 mm, maintained at 40° C. Elution with A: water+0.1% formic acid; B: acetonitrile+0.1% formic acid. Gradient:

| Gradient-Time | flow mL/min | % A | % B |
| --- | --- | --- | --- |
| 0.00 | 0.4 | 95 | 5 |
| 0.40 | 0.4 | 95 | 5 |

| Gradient-Time | flow mL/min | % A | % B |
| --- | --- | --- | --- |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 6

Phenomenex Gemini C18-reverse-phase column (250× 21.20 mm 5 μm particle size), elution with A: water+0.1% formic acid; B: CH₃CN+0.1% formic acid. Gradient—90% A/10% B to 2% A/98% B over 20 min—flow rate 18 mL/min. Detection—In-line UV detector set at 254 nM wavelength.

Example 1

1-(5-tert-Butyl-2-phenyl-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea

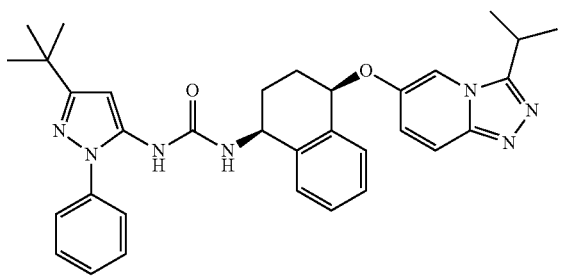 [SMILES: CC(C)c1nnc2ccc(O[C@@H]3CC[C@H](NC(=O)Nc4cc(C(C)(C)C)nn4-c4ccccc4)c4ccccc43)cn12]

a. 2,2,2-Trifluoro-N—(S)-1,2,3,4-tetrahydro-naphthalen-1-yl-acetamide (Intermediate 1a)

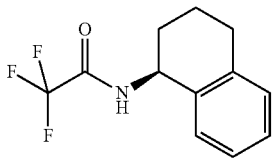 [SMILES: O=C(N[C@H]1CCCc2ccccc21)C(F)(F)F]

Ethyl trifluoroacetate (24.2 mL, 204 mmol) was added dropwise to a stirred solution of (S)-(1,2,3,4-tetrahydro-naphthalen-1-yl)amine (Alfa Aesar) (25.0 g, 170 mmol) and triethylamine (35.5 mL, 255 mmol) in methanol (250 mL) and the reaction stirred for 18 h. The mixture was concentrated to approximately ⅓ of its volume and then partitioned between DCM (200 mL) and water (200 mL). The aqueous layer was extracted into DCM (3×) and the combined organic layers were washed with brine, dried (MgSO₄) and concentrated in vacuo to yield the title compound (41.1 g, 169 mmol, 99%). ¹H NMR (400 MHz, CDCl₃): 1.80-1.95 (3H, m), 2.05-2.15 (1H, m), 2.75-2.90 (2H, m), 5.18-5.25 (1H, q, J 5.0 Hz), 6.38-6.48 (1H, br s), 7.12-7.16 (1H, m), 7.20-7.26 (3H, m).

b. 2,2,2-Trifluoro-N—((S)-4-oxo-1,2,3,4-tetrahydro-naphthalen-1-yl)-acetamide (Intermediate 1b)

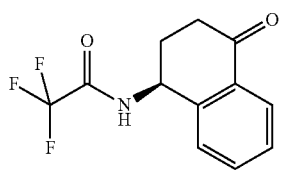 [SMILES: O=C1CC[C@H](NC(=O)C(F)(F)F)c2ccccc21]

Magnesium sulfate monohydrate (46.6 g, 338 mmol) in water (500 mL) was added to an ice cold solution of Intermediate 1a (41.1 g, 169 mmol) in acetone (1.0 L). Potassium permanganate (80.1 g, 507 mmol) was added portionwise (10.0 g portions) over a period of 45 min. The mixture was then stirred for 18 h. Sodium thiosulfate pentahydrate (126 g, 510 mmol) in water (400 mL) was added and the reaction stirred for 30 min. The mixture was concentrated to ~300 mL, then water (1.0 L), Celite (60 g) and EtOAc (1.0 L) were sequentially added. The mixture was thoroughly stirred, and then filtered through a pad of Celite. The aqueous layer was extracted into EtOAc (3×) and the combined organic layers washed with brine, dried (MgSO₄) and concentrated in vacuo to yield the title compound (36.6 g, 142 mmol, 84%). ¹H NMR (400 MHz, CDCl₃): 2.20-2.30 (1H, dddd, J 13.3, 10.0, 8.8, 4.5 Hz), 2.43-2.52 (1H, dddd, J 13.3, 7.2, 4.6, 4.6 Hz), 2.67-2.77 (1H, ddd, J 17.4, 10.1, 4.6 Hz), 2.78-2.88 (1H, ddd, J 17.4, 7.1, 4.6 Hz), 5.39-5.47 (1H, td, 8.5, 4.5 Hz), 7.32-7.37 (1H, d, J 7.7 Hz), 7.44-7.49 (1H, t, J 7.6 Hz), 7.59-7.64 (1H, td, J 7.6, 1.4 Hz), 8.03-8.07 (1H, dd, J 7.7, 1.4 Hz).

c. 2,2,2-Trifluoro-N-((1S,4R)-4-hydroxy-1,2,3,4-tetrahydro-naphthalen-1-yl)-acetamide (Intermediate 1c)

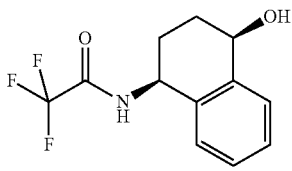 [SMILES: O=C(N[C@H]1CC[C@@H](O)c2ccccc21)C(F)(F)F]

Degassed DMF (argon sparged, 100 mL) was added to Intermediate 1b (8.00 g, 31.3 mmol) and [N-[(1R,2R)-2-(amino-κN)-1,2-diphenylethyl]-4-methylbenzenesulfonamidato-κN]chloro[(1,2,3,4,5,6-η)-1-methyl-4-(1-methylethyl)benzene]-ruthenium (Strem Chemicals Inc.: 594 mg, 0.93 mmol). Triethylamine (8.66 mL, 62.6 mmol) was added slowly to ice cold formic acid (2.34 mL, 62.6 mmol) and stirred for 20 min, this was then added to the DMF solution. The reaction was heated to 60° C. for 18 h. After cooling, the mixture was partitioned between DCM (200 mL) and water (600 mL). The aqueous layer was extracted DCM (3×) and the combined organic layers washed with brine, dried (MgSO₄) and concentrated in vacuo, then purified by FCC using 0-100% EtOAc in cyclohexane to yield the title compound (7.10 g, 27.4 mmol, 88%). ¹H NMR (400 MHz, CDCl₃): 1.88-1.92 (1H, d, J 4.8 Hz), 1.98-2.18 (4H, m), 4.80-4.88 (1H, m), 5.165-5.24 (1H, m), 6.70-6.80 (1H, br s), 7.25-7.30 (1H, m), 7.30-7.40 (2H, m), 7.45-7.50 (1H, m).

d. (1R,4S)-4-Amino-1,2,3,4-tetrahydro-naphthalen-1-ol (Intermediate 1d)

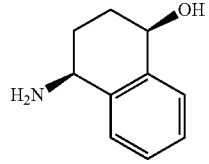 [SMILES: N[C@H]1CC[C@@H](O)c2ccccc21]

Sodium hydroxide (2.10 g, 53.0 mmol) was added to an ice cold solution of Intermediate 1c (3.43 g, 13.2 mmol) in methanol/water (2:1, 50 mL). The reaction was stirred for 3.5 h then passed through an SCX-2 cartridge, washing with MeOH and eluting with 2M $NH_3$ in MeOH, to yield the title compound (2.30 g, 13.2 mmol, 99%). $^1$H NMR (400 MHz, $d_6$-DMSO): 1.66-1.90 (4H, m), 3.71-3.77 (1H, t, J 5.4 Hz), 4.46-4.54 (1H, t, J 5.4 Hz), 7.14-7.22 (2H, m), 7.32-7.38 (1H, m), 7.40-7.46 (1H, m).

e. Isobutyric acid N'-(5-fluoro-pyridin-2-yl)-hydrazide (Intermediate 1e)

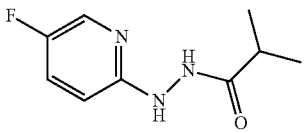

To a solution of 5-fluoro-2-hydrazinyl-pyridine (Prepared according to procedure described in WO2010022076; 2.08 g, 16.4 mmol), isobutyric acid (1.82 mL, 19.6 mmol), and HOBt hydrate (251 mg, 1.64 mmol) in DCM (50 mL) was added EDC (3.76 g, 19.6 mmol) and the resulting orange solution was stirred at room temperature for 18 h. Sat. aq. $NaHCO_3$ (50 mL) was added and the mixture was stirred vigorously for 15 min. The organics were washed with sat. aq. $NaHCO_3$ (50 mL), passed through a hydrophobic frit and concentrated under vacuum to leave a pale brown solid. The solid was suspended in $Et_2O$ (50 mL) and filtered, washing with $Et_2O$ (25 mL), to leave a white solid (1.48 g, 46%). The ethereal washings were concentrated under vacuum and the residue suspended in $Et_2O$ (10 mL), filtered, washed with $Et_2O$ (2×2 mL), to leave a white solid (330 mg, 10%). The solids were combined (1.81 g, 56%). $^1$H NMR (400 MHz, $CDCl_3$): 1.23 (6H, d), 2.50 (1H, sept), 6.65 (1H, dd), 6.80 (1H, d), 7.29 (1H, ddd), 7.77 (1H, br s), 8.01 (1H, d).

f. 6-Fluoro-3-isopropyl-[1,2,4]triazolo[4,3-a]pyridine (Intermediate 1f)

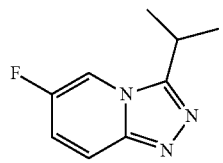

To a solution of Intermediate 1e (1.81 g, 9.18 mmol), triphenylphosphine (4.83 g, 18.4 mmol) and triethylamine (5.12 mL, 36.7 mmol) in THF (25 mL) at 0° C. was added hexachloroethane (4.36 g, 18.4 mmol) in 2 portions at a 1 min intervals. The resulting pale brown solution was allowed to warm to RT then stirred for 2 h. The resulting yellow suspension was filtered, washing with THF (2×25 mL). The combined organics were purified using SCX-2 cartridge (washed with DCM-MeOH (1:1, 100 mL) and MeOH (50 mL) and then the product was eluted with 2M $NH_3$ in MeOH) to give a pale yellow solid (1.60 g, 97%, contaminated with ~2.5% $Ph_3P=O$). $^1$H NMR (400 MHz, $CDCl_3$): 1.53 (6H, d), 3.32 (1H, sept), 7.15 (1H, ddd), 7.75 (1H, ddd), 7.84 (1H, m).

g. (1S,4R)-4-(3-Isopropyl-[1,2,4]triazolo[4,3-a]pyridin-6-yloxy)-1,2,3,4-tetrahydro-naphthalen-1-ylamine (Intermediate 1g)

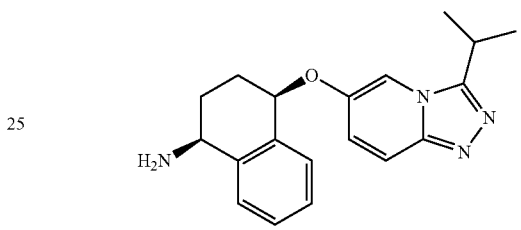

Intermediate 1d (634 mg, 3.88 mmol) was added portionwise to a suspension of sodium hydride (60% in mineral oil, 466 mg, 11.65 mmol) in dry DMF (5 mL) and the mixture stirred at room temperature for 20 min.

Intermediate 1f (535 mg, 2.99 mmol) was then added portionwise and the mixture heated at 60° C. for 4 h. The reaction was cooled, quenched with water and extracted with EtOAc (3×). The combined organic extracts were washed with brine and dried ($Na_2SO_4$), evaporated and purified by SCX-2 eluting with MeOH then 2M $NH_3$ in MeOH, to afford the title compound (274 mg, 79%). LCMS (Method 1): Rt 1.76 min, m/z 180 [MH$^+$].

h. 1-(5-tert-Butyl-2-phenyl-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea (Example 1)

A solution of Intermediate 1g (100 mg, 0.31 mmol) in dioxane (5 mL) with $EtNiPr_2$ (81.0 µL, 0.46 mmol) and (5-tert-butyl-2-phenyl-2H-pyrazol-3-yl)-carbamic acid 2,2,2-trichloro-ethyl ester (for reference procedure see WO2008016192; 185 mg, 0.46 mmol) was heated at 60° C. for 2 h. After cooling, the solution was purified by SCX-2 (eluting with MeOH then 2M $NH_3$ in MeOH) followed by HPLC (elution with 55-98% $H_2O$ in MeCN (0.1% $NH_3$)) to give the title compound as a colourless powder (120 mg, 69%). LCMS (Method 5): Rt 4.47 mins, m/z=564.2 [MH$^+$]. $^1$H NMR (400 MHz, $CDCl_3$): 1.32 (9H, s), 1.43-1.45 (3H, d, J 6.8 Hz), 1.47-1.50 (3H, d, J 6.8 Hz), 1.88-1.96 (1H, m), 2.00-2.16 (2H, m), 2.20-2.28 (1H, m), 3.16-3.30 (1H, sp, J 6.9 Hz), 5.04-5.16 (1H, m), 5.16-5.21 (1H, t, J 3.8 Hz), 5.38-5.46 (1H, d, J 8.8 Hz), 6.30 (1H, s), 6.51 (1H, s), 7.00-7.06 (1H, dd, J 9.9, 2.1 Hz), 7.22-7.34 (5H, m), 7.38-7.46 (3H, m), 7.52-7.62 (3H, m).

Example 2

1-Cyclopropyl-3-[(1S,4S)-4-(3-isopropyl-[1,2,4]triazolo[4,3-a]pyridin-6-yloxy)-1,2,3,4-tetrahydro-naphthalen-1-yl]-urea

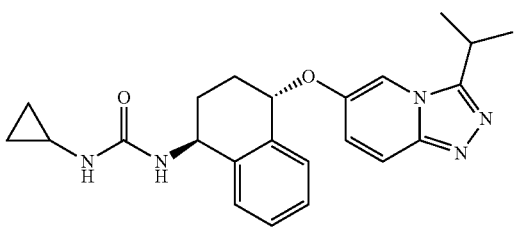 [SMILES: CC(C)c1nnc2ccc(O[C@H]3CC[C@H](NC(=O)NC4CC4)c4ccccc43)cn12]

a. 2,2,2-Trifluoro-N-((1S,4S)-4-hydroxy-1,2,3,4-tetrahydro-naphthalen-1-yl)-acetamide (Intermediate 2a)

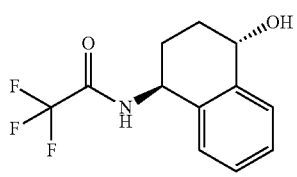 [SMILES: O=C(N[C@H]1CC[C@H](O)c2ccccc21)C(F)(F)F]

Argon was bubbled through a solution of Intermediate 1b (8.00 g, 31.1 mmol) and [N-[(1S,2S)-2-(amino-κN)-1,2-diphenylethyl]-4-methylbenzenesulfonamidato-κN]chloro[(1,2,3,4,5,6-η)-1-methyl-4-(1-methylethyl)benzene]-ruthenium (Strem Chemicals Inc.; 0.06 g, 0.93 mmol) in dry DMF (100 mL) for 10 min. A premixed combination of formic acid (2.4 mL, 62.2 mmol) and Et₃N (8.60 mL, 62.2 mmol) was added and the mixture stirred at 50° C. for 24 h. The mixture was cooled to room temperature and concentrated to ~25 mL. Water (70 mL) was added and the resulting precipitate filtered, and washed with DCM (3×30 mL) and diethyl ether (30 mL) to leave a solid (4.75 g). The filtrate was decanted to leave a dark solid. Subsequent purification by FCC using 0-30% EtOAc in cyclohexane gave a solid. This was combined with the first obtained solid to give a beige solid (5.93 g, 74%). $^1$H NMR (400 MHz, d$_6$-DMSO): 1.60-1.83 (2H, m), 2.06-2.17 (2H, m), 4.60 (1H, m), 5.08 (1H, m), 5.28 (1H, d), 7.07 (1H, m), 7.25 (1H, ddd), 7.28 (1H, ddd), 7.50 (1H, dd), 9.78 (1H, d).

b. (1S,4S)-4-Amino-1,2,3,4-tetrahydro-naphthalen-1-ol (Intermediate 2b)

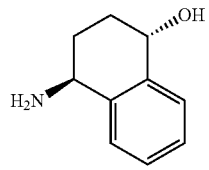

To a grey solution of Intermediate 2a (5.55 g, 21.4 mmol) in MeOH (50 mL) was added NaOH (1.28 g, 32.1 mmol) in water (15 mL) and the mixture stirred at room temperature for 3 days. NaOH (1.28 g, 32.1 mmol) was added and the brown solution was stirred for 5 h. The solution was applied directly to an SCX-2 column, washing with MeOH and eluting with 2M NH₃ in MeOH, and concentrated under vacuum to leave a grey solid. The solid was suspended in DCM (50 mL) with sonication, then filtered and dried under vacuum to leave a pale grey solid (2.93 g, 84%). $^1$H NMR (400 MHz, d$_6$-DMSO): 1.41-1.64 (2H, m), 2.02-2.13 (2H, m), 3.82 (1H, dd), 4.55 (1H, dd), 5.08 (1H, br s), 7.13-7.22 (2H, m), 7.35-7.49 (2H, m).

c. (1S,4S)-4-(3-Isopropyl-[1,2,4]triazolo[4,3-a]pyridin-6-yloxy)-1,2,3,4-tetrahydro-naphthalen-1-ylamine (Intermediate 2c)

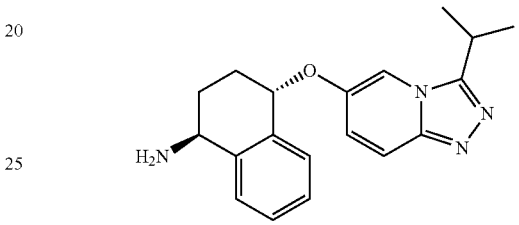

To a suspension of sodium hydride (60% in mineral oil, 1.07 g, 26.8 mmol) in dry DMF (20 mL) at room temperature under nitrogen was added Intermediate 2b (1.89 g, 11.6 mmol) portionwise over 2 min and the resulting brown solution was stirred for 20 min. Intermediate 1f (1.60 g, 8.93 mmol) was added and the solution stirred at 60° C. for 2 h. The dark brown solution was cooled to room temperature and concentrated under vacuum. The residue was purified by SCX-2, washing with MeOH (200 mL) and eluting with 2M NH₃ in MeOH, to leave a dark brown foam (3.21 g). Further purification by FCC using 2-10% [2M NH₃ in MeOH] in DCM, gave a brown foam (2.11 g, 76%). $^1$H NMR (400 MHz, d$_6$-DMSO): 1.37 (3H, d), 1.39 (3H, d), 1.59 (1H, m), 1.91 (1H, m), 2.11 (1H, m), 2.33 (1H, m), 3.58 (1H, sept), 3.96 (1H, dd), 5.55 (1H, dd), 7.18-7.37 (4H, m), 7.51 (1H, d), 7.68 (1H, d), 8.20 (1H, d).

d. 1-Cyclopropyl-3-[(1S,4S)-4-(3-isopropyl-[1,2,4]triazolo[4,3-a]pyridin-6-yloxy)-1,2,3,4-tetrahydro-naphthalen-1-yl]-urea (Example 2)

To a cloudy orange solution of Intermediate 2c (93.5 mg, 0.29 mmol) and DIPEA (63 μL, 0.363 mmol), in THF (4 mL) was added cyclopropyl-carbamic acid 4-nitro-phenyl ester (For reference procedure see WO2007/72158; 77.4 mg, 0.348 mmol). The resulting clear orange solution was stirred at room temperature for 10 min and then at 80° C. for 3 h. After cooling, the mixture was concentrated under vacuum to leave a brown residue. Purification by FCC (5-20% MeOH in EtOAc) gave a brown glass that was triturated (diethyl ether) to leave a pale yellow solid (64.7 mg, 55%). Further purification by HPLC (10-95% MeCN in water, 0.1% HCO₂H) gave a pale yellow solid (42.2 mg, 30%). LCMS (Method 5): Rt 3.13 mins, m/z 406 [MH⁺] $^1$H NMR (400 MHz, CDCl₃): 0.34 (2H, m), 0.57 (2H, m), 1.37 (3H, d), 1.39 (3H, d), 1.74 (1H, m), 1.97 (1H, m), 2.10 (1H, m), 2.22 (1H, m), 2.47 (1H, m), 3.57 (1H, sept), 4.90 (1H, m), 5.57 (1H, dd), 6.05 (1H, d), 6.18 (1H, d), 7.23 (1H, dd), 7.25-7.37 (3H, m), 7.39 (1H, d), 7.68 (1H, d), 8.21 (1H, d).

Example 3

(±)-trans-1-(5-tert-Butyl-2-p-tolyl-2H-pyrazol-3-yl)-3-[3-(3-isopropyl-[1,2,4]triazolo[4,3-a]pyridin-6-ylsulfanyl)-indan-1-yl]-urea

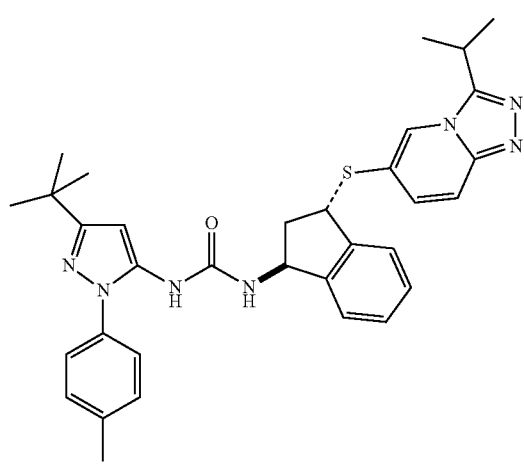

a. (±)-3-tert-Butylsulfanyl-indan-1-one (Intermediate 3a)

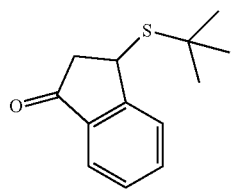

To a solution of 3-bromo-indan-1-one (6.6 g, 31 mmol) in THF (25 mL), tert-butanethiol (7.0 mL, 62 mmol) followed by DIPEA (dropwise addition; 10.6 mL, 62 mmol) were added at 0° C. The mixture was stirred at 0° C. for 45 min, then allowed to warm to RT for 1 h, and then heated at 50° C. for 90 min. The mixture was concentrated and azeotroped with toluene, partitioned between Et$_2$O/water and extracted with Et$_2$O. Combined organic extracts were dried (Na$_2$SO$_4$) and evaporated. Purification by FCC, using 0-16% EtOAc in cyclohexane as eluent, gave the title compound as a pale yellow solid (3.6 g). $^1$H NMR (400 MHz, CDCl$_3$): 1.47 (9H, s), 2.86 (1H, dd, J 3.4 19.0 Hz), 3.28 (1H, dd, J 3.3, 19.0 Hz), 4.46-4.52 (1H, m), 7.38-7.46 (1H, m), 7.61-7.67 (1H, m), 7.69-7.75 (2H, m).

b. (±)-cis-3-tert-Butylsulfanyl-indan-1-ol (Intermediate 3b)

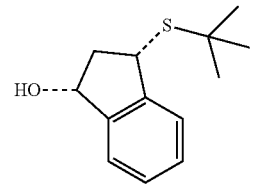

A solution of Intermediate 3a (3.5 g, 15.9 mmol) was formed in MeOH (90 mL) and cooled to 0° C. Sodium borohydride (608 mg, 16 mmol) was added and the mixture stirred at 0° C. for 40 mins. The reaction was quenched by the addition of AcOH (2 mL) then evaporated to give a white solid. The residue was partitioned between EtOAc and sat. NaHCO$_3$ solution (aq) and then extracted with EtOAc. The combined organics were dried (Na$_2$SO$_4$), filtered, evaporated then purified by FCC, using 6-30% EtOAc in cyclohexane as eluent, to give the title compound as a white solid (2.9 g). $^1$H NMR (400 MHz, CDCl$_3$): 1.46 (9H, s), 2.10-2.19 (1H, m), 2.97-3.07 (1H, m), 4.14-4.21 (1H, m), 5.11-5.17 (1H, m), 7.27-7.36 (2H, m), 7.41-7.48 (2H, m).

c. (±)-trans-2-(3-tert-butylsulfanyl-indan-1-yl)-isoindole-1,3-dione (Intermediate 3c)

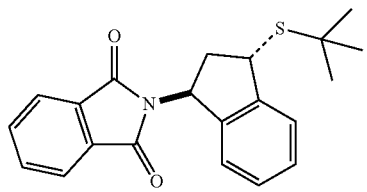

A solution of Intermediate 3b (2.9 g, 13.1 mmol), phthalimide (2.3 g, 15.7 mmol) and triphenylphosphine (4.1 g, 15.7 mmol) in THF (100 mL) was stirred at 0° C. DIAD (3.08 mL, 15.7 mmol) was added dropwise and the mixture allowed to warm to RT overnight. Water (10 drops) was added and then evaporated to dryness. Purification by FCC, using 0-12% EtOAc in cyclohexane as eluent, gave the title compound as an off white solid (2.98 g).). LCMS (Method 2): Rt 4.45 min, m/z 262 [(M-S$^t$Bu)$^+$].

d. (±)-trans-2-[3-(2-nitro-phenyldisulfanyl)-indan-1-yl]-isoindole-1,3-dione (Intermediate 3d)

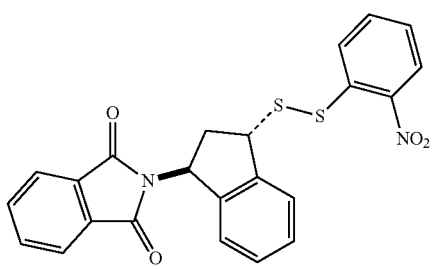

To a suspension of Intermediate 3c (600 mg, 1.71 mmol) in AcOH (3 mL), 2-nitrobenzenesulfenyl chloride (342 mg, 1.8 mmol) was added, giving a dark yellow solution. After stirring at RT for 30 mins, the resulting precipitate was filtered and washed with 1:1 Et$_2$O/cyclohexane then cyclohexane and dried under vacuum to give the title compound with 1 eq AcOH as an off white solid (355 mg). $^1$H NMR (400 MHz, CDCl$_3$): 2.61-2.70 (1H, m), 2.96-3.06 (1H, m), 4.86-4.90 (1H, m), 6.06 (1H, t, J 7.7 Hz), 7.03-7.08 (1H, m), 7.17-7.23 (2H, m), 7.29-7.26 (1H, m), 7.41-7.45 (1H, m), 7.61-7.67 (1H, m), 7.69-7.74 (2H, m), 7.78-7.84 (2H, m), 8.19-8.27 (2H, m).

e. (±)-trans-2-(3-Mercapto-indan-1-yl)-isoindole-1,3-dione (Intermediate 3e)

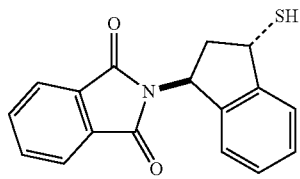

To a suspension of Intermediate 3d (396 mg, 0.78 mmol) in MeOH (16 mL), potassium carbonate (400 mg, 2.3 mmol) and dithiothreitol (160 mg, 1.0 mmol) were added. The mixture was stirred at RT for 30 mins. KH$_2$PO$_4$ (800 mg) was added followed by AcOH (30 drops). The mixture was partitioned between EtOAc/water, extracted with EtOAc and the combined organics were dried (Na$_2$SO$_4$), and evaporated. Purification by FCC, using 3-5% EtOAc in cyclohexane as eluent, gave the title compound as a yellow gum (158 mg). $^1$H NMR (400 MHz, CDCl$_3$): 2.45-2.55 (1H, m), 3.00-3.09 (1H, m), 4.90-4.98 (1H, m), 6.00-6.05 (1H, m), 7.10-7.14 (1H, m), 7.18-7.24 (1H, m), 7.30-7.36 (1H, m), 7.45-7.48 (1H, m), 7.68-7.75 (2H, m), 7.78-7.84 (2H, m).

f. (±)-trans-2-[3-(3-Isopropyl-[1,2,4]triazolo[4,3-a]pyridin-6-ylsulfanyl)-indan-1-yl]-isoindole-1,3-dione (Intermediate 3f)

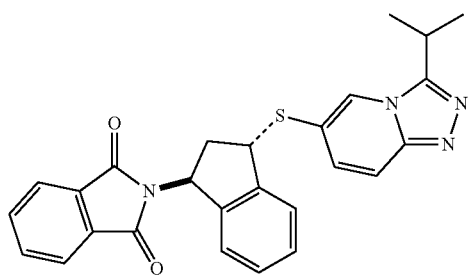

A solution of Intermediate 3e (104 mg, 0.35 mmol) and 6-iodo-3-isopropyl-[1,2,4]triazolo[4,3-a]pyridine (For a reference procedure see WO2010094956; 101 mg, 0.35 mmol) in dry DMF (1 mL) was degassed with argon. Cs$_2$CO$_3$ (172 mg, 0.53 mmol) and Pd(dppf)Cl$_2$.DCM (57 mg, 0.07 mmol) were added and the mixture heated to 90° C. overnight. The mixture was evaporated to dryness, partitioned between DCM/water and extracted with DCM. The combined organics were dried (Na$_2$SO$_4$), filtered, evaporated then purified by FCC using 0-8% MeOH in DCM as eluent. The residue was re-purified by FCC, using 10-80% EtOAc in DCM as eluent, to give the title compound (37 mg). LCMS (Method 2): Rt 3.45 min, m/z 455 [MH$^+$].

g. (±)-trans-3-(3-Isopropyl-[1,2,4]triazolo[4,3-a]pyridin-6-ylsulfanyl)-indan-1-ylamine (Intermediate 3 g)

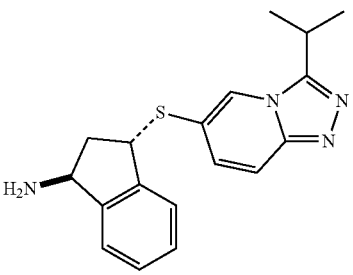

A solution of Intermediate 3f (37 mg, 0.08 mmol) was formed in MeOH (10 mL). Hydrazine monohydrate (250 μL) was added and the mixture stirred at RT over night. Evaporated to dryness and purified by FCC using 0-6% (9:1 MeOH/NH$_3$ aq) in DCM as eluent to give the title compound (15 mg). LCMS (Method 1): Rt 1.94 min, m/z 325 [MH$^+$]

h. (±)-trans-1-(5-tert-Butyl-2-p-tolyl-2H-pyrazol-3-yl)-3-[3-(3-isopropyl-[1,2,4]triazolo[4,3-a]pyridin-6-ylsulfanyl)-indan-1-yl]-urea Example 3

The title compound was prepared using Intermediate 3g and (5-tert-Butyl-2-p-tolyl-2H-pyrazol-3-yl)-carbamic acid 2,2,2-trichloro-ethyl ester (Synthetic Communications, 39(22), 3999-4009; 2009) by using an analogous procedure to that described in Example 1 step h. LCMS (Method 5): Rt 4.94 min, m/z 580 [MH$^+$]. $^1$H NMR (300 MHz, CDCl$_3$): 1.30 (9H, s), 1.43 (6H, dd, J 10.3, 6.9 Hz), 2.12-2.22 (1H, m), 2.36 (3H, s), 2.63-2.71 (1H, m), 3.17-3.26 (1H, m), 4.61-4.65 (1H, m), 5.15 (1H, d, J 8.2 Hz), 5.43-5.51 (1H, m), 6.22 (1H, s), 6.31 (1H, s), 6.99 (1H, d, J 6.9 Hz), 7.09 (1H, d, J 7.1 Hz), 7.15-7.27 (5H, m), 7.33-7.37 (2H, m), 5.57-7.61 (1H, m), 7.75 (1H, m).

Example 4

1-(5-tert-Butyl-2-p-tolyl-2H-pyrazol-3-yl)-3-[(1S,4R)-4-{3-[3-(2-morpholin-4-yl-ethoxy)-phenyl]-[1,2,4]triazolo[4,3-a]pyridin-6-yloxy}-1,2,3,4-tetrahydro-naphthalen-1-yl]-urea

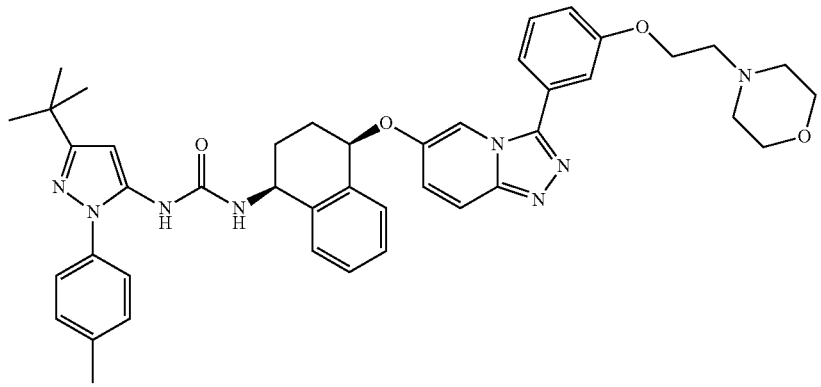 [SMILES: Cc1ccc(-n2nc(C(C)(C)C)cc2NC(=O)N[C@H]2CC[C@@H](Oc3ccc4nnc(-c5cccc(OCCN6CCOCC6)c5)n4c3)c3ccccc32)cc1]

a. N-(5-fluoro-pyridin-2-yl)-N'-[1-[3-(2-morpholin-4-yl-ethoxy)-phenyl]-methylidine]-hydrazine (Intermediate 4a)

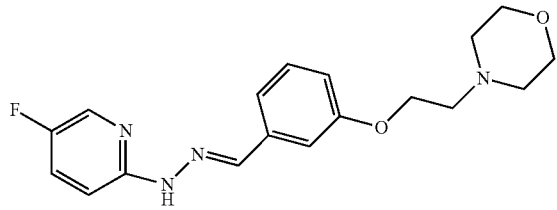 [SMILES: Fc1ccc(N/N=C/c2cccc(OCCN3CCOCC3)c2)nc1]

5-fluoro-2-hydrazinyl-pyridine (for reference procedure see WO2010022076; 9.2 g, 0.072 mol) was added to 3-(2-morpholin-4-yl-ethoxy-benzaldehyde (for reference procedure see WO2628448; 17.0 g, 0.073 mol) in ethanol (175 mL) and the mixture stirred for 1 h. The resulting precipitate was filtered off to give the title compound as a beige coloured solid (19.46 g, 79%) LCMS (Method 2): Rt 2.33 min, m/z 345 [MH+].

b. 6-Fluoro-3-[3-(2-morpholin-4-yl-ethoxy)-phenyl]-[1,2,4]triazolo[4,3-a]pyridine (Intermediate 4b)

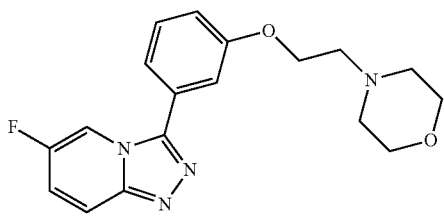 [SMILES: Fc1ccc2nnc(-c3cccc(OCCN4CCOCC4)c3)n2c1]

Ethanol (10 mL) was added to a solution of Intermediate 4a and (diacetoxyiodo)benzene (7.9 g, 0.024 mol) in dichloromethane (60 mL) and the mixture stirred at room temperature for 3 h. The solvent was evaporated and the residue purified by FCC, using 0-20% MeOH in DCM, to give a brown oil. This was dissolved in dichloromethane and washed with NaHCO₃, dried (MgSO₄) and evaporated to yield the title compound as beige coloured solid (4.1 g, 69%). LCMS (Method 2): Rt 0.28 min, m/z 343 [MH+].

c. (1S,4R)-4-{3-[3-(2-Morpholin-4-yl-ethoxy)-phenyl]-[1,2,4]triazolo[4,3-a]pyridin-6-yloxy}-1,2,3,4-tetrahydro-naphthalen-1-ylamine (Intermediate 4c)

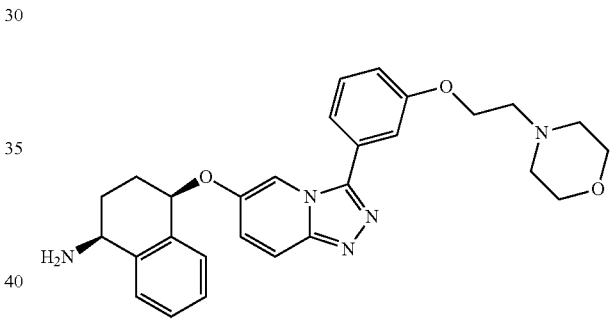

The title compound was prepared starting from Intermediate 4b and Intermediate 1d with a similar procedure to that described in Example 1 step g. LCMS (Method 1): Rt 1.68 min, m/z 486 [MH+].

d. 1-(5-tert-Butyl-2-p-tolyl-2H-pyrazol-3-yl)-3-((1S,4R)-4-{3-[3-(2-morpholin-4-yl-ethoxy)-phenyl]-[1,2,4]triazolo[4,3-a]pyridin-6-yloxy}-1,2,3,4-tetrahydro-naphthalen-1-yl]-urea. (Example 4)

The title compound was prepared starting from Intermediate 4c and (5-tert-butyl-2-p-tolyl-2H-pyrazol-3-yl)-carbamic acid 2,2,2-trichloro-ethyl ester (Synthetic Communications, 39(22), 3999-4009; 2009) with a similar procedure to that described in Example 1 step h. LCMS (Method 5): Rt 3.94 min, m/z 741 [MH+]. ¹H NMR (400 MHz, CDCl₃): 1.32 (9H, s), 1.84-1.94 (1H, m), 1.98-2.09 (2H, m), 2.17-2.24 (1H, m), 2.36 (3H, s), 2.56 (4H, m), 2.83 (2H, t, J 5.62 Hz), 3.68 (4H, t, J 4.59 Hz), 4.18 (2H, t, J 5.63 Hz), 5.03-5.09 (1H, m), 5.17-5.22 (2H, m), 6.27 (2H, s), 7.07 (1H, dd, J 2.51 8.32 Hz), 7.13 (1H, dd J 2.15, 9.92, Hz), 7.21-7.39 (11H, m), 7.46 (1H, t), 7.74 (1H, d, J 10.09 Hz), 7.87 (1H, s).

Example 5

1-(5-tert-Butyl-2-p-tolyl-2H-pyrazol-3-yl)-3-[(1S,4R)-4-(3-isopropyl-[1,2,4]triazolo[4,3-a]pyridin-7-yloxy)-1,2,3,4-tetrahydro-naphthalen-1-yl]-urea

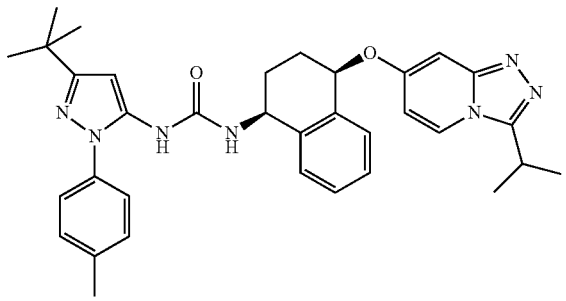 [SMILES: Cc1ccc(-n2nc(C(C)(C)C)cc2NC(=O)N[C@H]2CC[C@@H](Oc3ccn4c(C(C)C)nnc4c3)c3ccccc32)cc1]

a. (1S,4R)-4-(2-Fluoro-pyridin-4-yloxy)-1,2,3,4-tetrahydro-naphthalen-1-ylamine (Intermediate 5a)

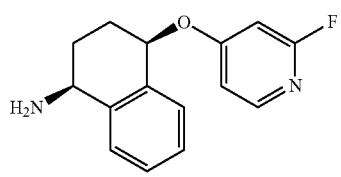 [SMILES: N[C@H]1CC[C@@H](Oc2ccnc(F)c2)c2ccccc21]

A solution of Intermediate 1d (400 mg, 2.45 mmol) was formed in THF (10 mL). Sodium Hydride (60% in mineral oil, 118 mg, 2.94 mmol) was added and the mixture was stirred at RT for 15 minutes. A solution of 2,4-difluoropyridine (338 mg, 2.94 mmol) in THF (1 mL) was added and the mixture was stirred at RT for 2 h. Further Sodium hydride (60% in mineral oil, 100 mg, 2.5 mmol) was added and the mixture stirred at RT for 1 h. The reaction mixture was quenched cautiously with water then partitioned between water and EtOAc. The aqueous layer was extracted with EtOAc and the combined organic phases were dried (sodium sulphate), filtered and evaporated. Purification by FCC, using 0-10% MeOH in DCM as eluent, gave the crude title compound as a brown oil (500 mg). LCMS (Method 1): Rt 0.32, 1.83, 2.05 min, m/z 259 [MH$^+$].

b. [(1S,4R)-4-(2-Fluoro-pyridin-4-yloxy)-1,2,3,4-tetrahydro-naphthalen-1-yl]-carbamic acid tert-butyl ester (Intermediate 5b)

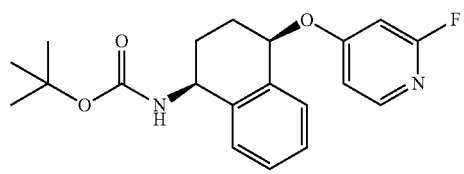 [SMILES: CC(C)(C)OC(=O)N[C@H]1CC[C@@H](Oc2ccnc(F)c2)c2ccccc21]

A solution of Intermediate 5a (500 mg, 1.9 mmol) was formed in DCM (20 mL). Triethylamine (290 µL, 2.1 mmol) followed by Boc-anhydride (465 mg, 2.1 mmol) were added and the mixture stirred at RT for 4 h. The mixture was partitioned between DCM/water and the phases were separated through a Isolute phase-separation cartridge. The organic phase was evaporated then purified by FCC, using 0-50% EtOAc/c-hexane as eluent, to give the crude title compound as a brown oil (300 mg). LCMS (Method 1): Rt 3.83 min, m/z 359 [MH$^+$].

c. [(1S,4R)-4-(2-Hydrazino-pyridin-4-yloxy)-1,2,3,4-tetrahydro-naphthalen-1-yl]-carbamic acid tert-butyl ester (Intermediate 5c)

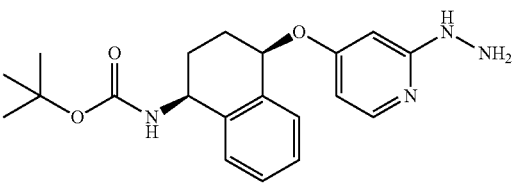 [SMILES: CC(C)(C)OC(=O)N[C@H]1CC[C@@H](Oc2ccnc(NN)c2)c2ccccc21]

A solution of Intermediate 5b (300 mg, 0.84 mmol) was formed in IMS (5 mL). Hydrazine monohydrate (5 mL) was added and the mixture heated in a sealed tube at 80° C. overnight. The mixture was concentrated and partitioned between EtOAc/water, extracted with EtOAc and the combined organics were dried (Na$_2$SO$_4$), filtered and evaporated to give the crude title material as a yellow foam (300 mg). LCMS (Method 4): Rt 2.17 min, m/z 371 [MH$^+$].

d. {(1S,4R)-4-[2-(N'-Isobutyryl-hydrazino)-pyridin-4-yloxy]-1,2,3,4-tetrahydro-naphthalen-1-yl}-carbamic acid tert-butyl ester (Intermediate 5d)

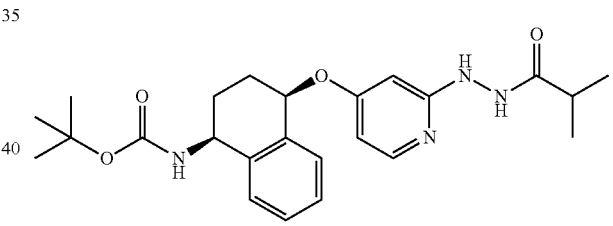

A solution of Intermediate 5c (300 mg, 0.81 mmol) was formed in DCM (10 mL). Triethylamine (170 µL, 1.20 mmol) and iso-butyryl chloride (102 µL, 0.97 mmol) were added and the mixture stirred at RT for 2 h. Partitioned between DCM/water and separated using a phase-separation cartridge and evaporated. Purification by FCC, using 0-100% EtOAc in cyclohexane as eluent, gave the crude title compound as a yellow solid (150 mg). LCMS (Method 1): Rt 2.49 min, m/z 441 [MH$^+$].

e. [(1S,4R)-4-(3-Isopropyl-[1,2,4]triazolo[4,3-a]pyridin-7-yloxy)-1,2,3,4-tetrahydro-naphthalen-1-yl]-carbamic acid tert-butyl ester (Intermediate 5e)

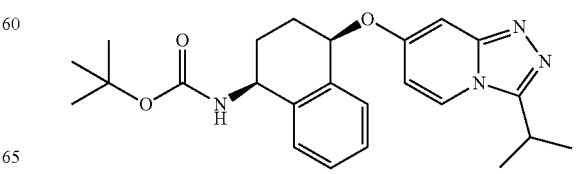

A solution of Intermediate 5d (150 mg, 0.34 mmol) was formed in THF (10 mL). Triethylamine (188 µL, 1.36 mmol) and triphenylphosphine (179 mg, 0.68 mmol) were added and the mixture cooled in an ice-bath. Hexachloroethane (160 mg, 0.68 mmol) was added and the mixture stirred at 0° C. for 10 min then allowed to warm to RT overnight. Additional triethylamine (188 µL, 1.36 mmol), triphenylphosphine (179 mg, 0.68 mmol) and hexachloroethane (160 mg, 0.68 mmol) were added and the mixture heated at 50° C. for 1 h. After cooling, the mixture was partitioned between EtOAc/water, then extracted with EtOAc. The combined organics were dried (Na$_2$SO$_4$), filtered and evaporated then purified by FCC, using 0-10% MeOH in EtOAc as eluent, to give the title material as an off white solid (110 mg). LCMS (Method 1): Rt 2.79 min, m/z 423 [MH$^+$].

f. (1S,4R)-4-(3-Isopropyl-[1,2,4]triazolo[4,3-a]pyridin-7-yloxy)-1,2,3,4-tetrahydro-naphthalen-1-ylamine (Intermediate 5f)

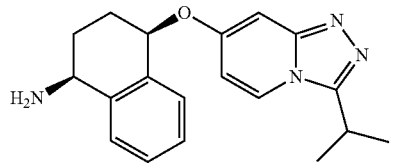 [SMILES: CC(C)c1nnc2cc(O[C@@H]3CC[C@H](N)c4ccccc43)ccn12]

A solution of Intermediate 5e (110 mg, 0.26 mmol) was formed in DCM (6 mL). TFA (3 mL) was added and the mixture stirred at RT for 1 h. Purification using an SCX-2 cartridge, washing with MeOH then eluting with 2M NH$_3$ in MeOH, gave the crude title compound as a brown foam (80 mg). LCMS (Method 1): Rt 0.31, 1.55 min, m/z 323 [MH$^+$].

g. 1-(5-tert-Butyl-2-p-tolyl-2H-pyrazol-3-yl)-3-[(1S,4R)-4-(3-isopropyl-[1,2,4]triazolo[4,3-a]pyridin-7-yloxy)-1,2,3,4-tetrahydro-naphthalen-1-yl]-urea (Example 5)

The title compound was prepared starting from Intermediate 5f and (5-tert-butyl-2-p-tolyl-2H-pyrazol-3-yl)-carbamic acid 2,2,2-trichloro-ethyl ester (Synthetic Communications, 39(22), 3999-4009; 2009) with a similar procedure to that described in Example 1 step h. LCMS (Method 5): Rt 4.27 min, m/z 578 [MH$^+$]. $^1$H NMR (400 MHz, d$_6$-DMSO): 1.27 (9H, s), 1.36 (6H, dd, J 2.5 7.0 Hz), 1.77-1.86 (1H, m), 1.93-2.01 (1H, m), 2.03-2.17 (2H, m), 2.36 (3H, s), 3.43-3.53 (1H, m), 4.79-4.85 (1H, m), 5.69 (1H, t, J 4.5 Hz), 6.33 (1H, s), 6.63 (1H, dd, J 2.5, 7.4 Hz), 7.10 (1H, d, J 8.7 Hz), 7.27-7.38 (9H, m), 8.03 (1H, s), 8.34 (1H, d, J 7.4 Hz).

Example 6

1-{5-tert-Butyl-2-[3-(2-morpholin-4-yl-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea

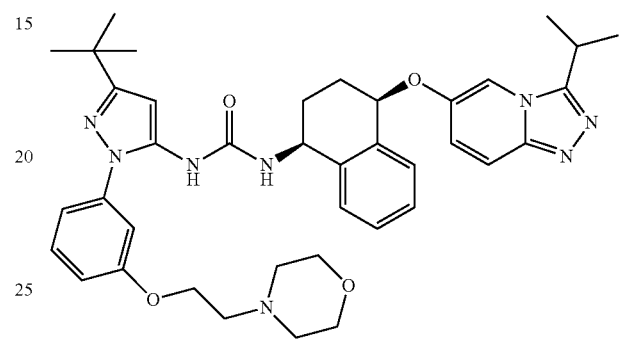

a. 5-tert-Butyl-2-[3-(2-morpholin-4-yl-ethoxy)-phenyl]-2H-pyrazol-3-ylamine (Intermediate 6a)

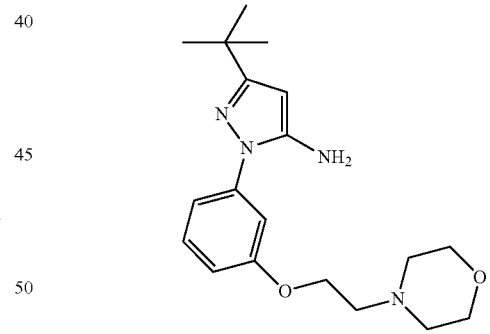

DIAD (847 µL, 4.32 mmol) was added slowly to a solution of 3-(5-amino-3-tert-butyl-1H-pyrazol-1-yl)phenol (For reference procedure see US2006/35922; 500 mg, 2.16 mmol), 4-(2-hydroxyethyl)morpholine (394 µl, 3.25 mmol) and triphenylphosphine (1.13 g, 4.32 mmol) in THF (10.0 mL) and stirred for 72 h. The reaction mixture was partitioned between EtOAc (75 mL) and H$_2$O (75 mL) and the aqueous layer extracted with EtOAc (3×). The combined organic layers were dried (MgSO$_4$), filtered and evaporated in vacuo and purified by FCC, using 0.5-6% [2M NH$_3$ in MeOH] in DCM to give semi-pure title compound (526 mg). This was progressed to the next reaction without further purification. LCMS (Method 4): Rt 0.28 min, m/z 345 [MH$^+$].

b. {5-tert-Butyl-2-[3-(2-morpholin-4-yl-ethoxy)-phenyl]-2H-pyrazol-3-yl}-carbamic acid 2,2,2-trichloro-ethyl ester (Intermediate 6b)

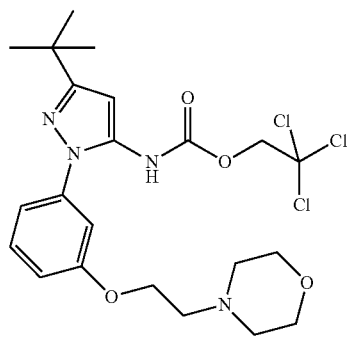 [SMILES: CC(C)(C)c1cc(NC(=O)OCC(Cl)(Cl)Cl)n(-c2cccc(OCCN3CCOCC3)c2)n1]

Intermediate 6a (75.0 mg, 0.22 mmol) was dissolved in THF (2.0 mL) and cooled in an ice/water bath. Diisopropylethylamine (76 µL, 0.44 mmol) was added followed by 2,2,2-trichloroethylchloroformate (30 µL, 0.22 mmol). After 30 minutes the ice bath was removed and the reaction warmed to room temperature overnight. The reaction mixture was partitioned between EtOAc (50 mL) and H₂O (50 mL) and the aqueous layer extracted with EtOAc (3×). The combined organic layers were dried (MgSO₄), filtered and evaporated in vacuo to yield the title compound (115 mg, 0.22 mmol, 99%). LCMS (Method 4): Rt 2.53 min, m/z 521 [MH⁺].

c. 1-{5-tert-Butyl-2-[3-(2-morpholin-4-yl-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]urea (Example 6)

The title compound was prepared starting from Intermediate 6b and Intermediate 1g with a similar procedure to that described in Example 1 step h. LCMS (Method 5): Rt 3.41 min, m/z=693 [MH⁺]. ¹H NMR (400 MHz, CDCl₃): 1.30 (9H, s), 1.41-1.45 (3H, d, J 6.9 Hz), 1.45-1.48 (3H, d, J 6.9 Hz), 1.88-1.98 (1H, m), 2.00-2.12 (2H, m), 2.18-2.28 (1H, m), 2.52-2.58 (4H, t, J 4.6 Hz), 2.76-2.82 (2H, t, J 5.6 Hz), 3.17-3.28 (1H, sp, J 6.9 Hz), 3.64-3.68 (4H, t, J 4.7 Hz), 4.10-4.14 (2H, t, J 5.5 Hz), 5.03-5.10 (1H, td, J 9.0, 5.4 Hz), 5.14-5.18 (1H, t, J 7.9), 5.52-5.58 (1H, br d, J 8.7 Hz), 6.30 (1H, s), 6.63 (1H, s), 6.82-6.86 (1H, dd, J 8.5, 2.5 Hz), 6.99-7.03 (1H, dd, J 9.9, 2.0 Hz), 7.05-7.07 (1H, t, J 2.1 Hz), 7.07-7.10 (1H, d, J 7.8 Hz), 7.23-7.31 (5H, m), 7.40-7.42 (1H, d, J 1.8 Hz), 7.56-7.60 (1H, d, J 9.8 Hz).

Example 7

1-(5-tert-Butyl-2-p-tolyl-2H-pyrazol-3-yl)-3-{(1S,4R)-4-(3-(2-hydroxy-phenyl)-[1,2,4]triazolo[4,3-a]pyridin-6-yloxy)-1,2,3,4-tetrahydro-naphthalen-1-yl}-urea

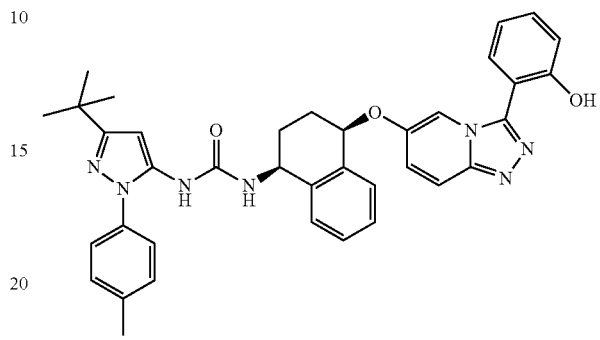

A solution of Example 24 (150 mg, 0.21 mmol) in ethanol (5 mL) was hydrogenolysed over palladium hydroxide (20% on carbon; 50 mg) at room temperature under hydrogen overnight. The catalyst was filtered off through Celite and the filtrate evaporated. The residue was purified by HPLC (Method 6). Product containing fractions were freeze dried to give the title compound as colourless solid. LCMS (Method 5): Rt 4.77 min, m/z 628 [MH⁺]. II NMR (400 MHz, CDCl₃): 1.32 (9H, s), 1.85-1.94 (1H, m), 2.02-2.11 (2H, m), 2.23-2.30 (1H, m), 2.36 (3H, s), 5.04-5.12 (2H, m), 5.25 (1H, m), 6.18 (1H, br s), 6.25 (1H, s), 7.00-7.04 (1H, m), 7.17-7.26 (6H, m), 7.29-7.33 (3H, m), 7.36-7.40 (3H, m), 7.59 (1H, dd, J 1.72, 7.80 Hz), 7.77 (1H, d, J 9.92 Hz), 8.09 (1H, d, J 1.45, Hz).

Example 8

1-(5-tert-Butyl-isoxazol-3-yl)-3-[(1S,3S)-3-(3-isopropyl-[1,2,4]triazolo[4,3-a]pyridin-6-yloxy)-indan-1-yl]-urea

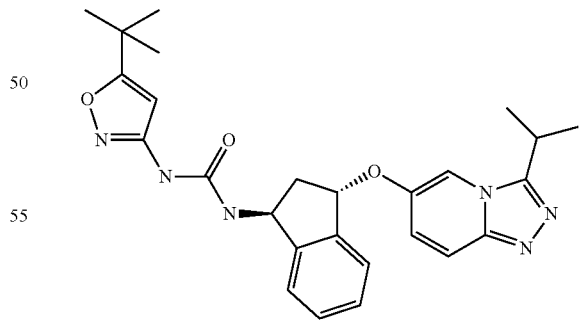

The title compound was prepared starting from (1S,3S)-3-amino-indan-1-ol (Chemistry Letters, 2002, 3, 266-267) and 5-tert-butyl-isoxazol-3-ylamine (Alfa Aesar) with similar procedures to that described in Example 1, steps g and h, and Example 6 step b. LCMS (Method 5): Rt 4.23 min, m/z 578 [MH⁺]. ¹H NMR (400 MHz, CDCl₃): 1.28 (9H, s), 1.48 (6H, dd, J 9.62 and 6.89 Hz), 2.35 (1H, m), 2.89 (1H, m), 3.26 (1H, m), 5.68-5.76 (3H, m), 7.05 (1H, dd, J 9.87 and 2.06), 7.29-7.34 (2H, m), 7.35-7.41 (2H, m), 7.48 (1H, m), 7.68 (2H, m), 7.76 (1H, m).

Example 9

N-(4-{(1R,4S)-4-[3-(5-tert-Butyl-2-p-tolyl-2H-pyrazol-3-yl)-ureido]-1,2,3,4-tetrahydro-naphthalen-1-yloxymethyl}-pyridin-2-yl)-2-methoxy-acetamide

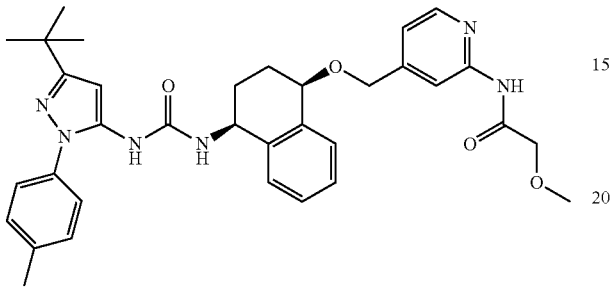

a. ((1S,4R)-4-Hydroxy-1,2,3,4-tetrahydro-naphthalen-1-yl)-carbamic acid tert-butyl ester (Intermediate 9a)

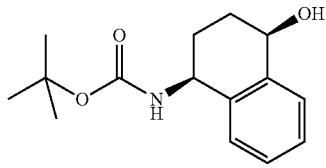 [SMILES: CC(C)(C)OC(=O)N[C@H]1CC[C@@H](O)c2ccccc21]

Intermediate 1d (1.35 g, 8.28 mmol) was suspended in acetonitrile (40 mL) then di-tert-butyl-dicarbonate (1.99 g, 9.11 mmol) was added. The mixture was stirred at room temperature for 22 h and then evaporated to dryness. Purification by FCC, eluting with 0-75% ethyl acetate in cyclohexane, gave the title compound as a white foam (2.12 g, 97%). LCMS (Method 3): Rt 3.31 min, m/z 286 [MNa$^+$].

b. [(1S,4R)-4-(2-Amino-pyridin-4-ylmethoxy)-1,2,3,4-tetrahydro-naphthalen-1-yl]-carbamic acid tert-butyl ester (Intermediate 9b)

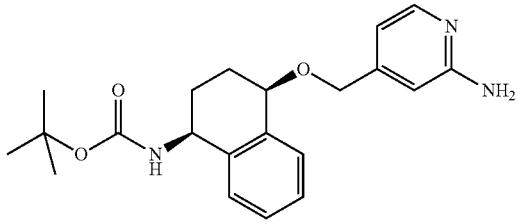 [SMILES: CC(C)(C)OC(=O)N[C@H]1CC[C@@H](OCc2ccnc(N)c2)c2ccccc21]

Intermediate 9a (1.47 g, 5.59 mmol) was dissolved in dry DMF (15 mL) under argon and cooled in an ice bath. To this was added sodium hydride (60% in mineral oil, 224 mg, 5.59 mmol) and stirred for 10 min. Additional sodium hydride (60% in mineral oil, 224 mg, 5.59 mmol) was added followed immediately by 2-amino-4-bromomethylpyridine hydrobromide (for reference procedure see Bioorg. Med. Chem. Letts, 2011, 21, 4, 1232) (1.50 g, 5.59 mmol). Mixture stirred with cooling under argon for 1 h. The reaction mixture was diluted with water and extracted with DCM (4×30 mL). The combined organic layers were washed with brine, dried (Na$_2$SO$_4$), and evaporated. The residue was purified by FCC, eluting with 0-10% MeOH in DCM, to give the title compound as a white foam (1.37 g, 66%). LCMS (Method 3): Rt 2.60 min, m/z 370.2 [MH$^+$]

c. {(1S,4R)-4-[2-(2-Methoxy-acetylamino)-pyridin-4-ylmethoxy]-1,2,3,4-tetrahydro-naphthalen-1-yl}-carbamic acid tert-butyl ester (Intermediate 9c)

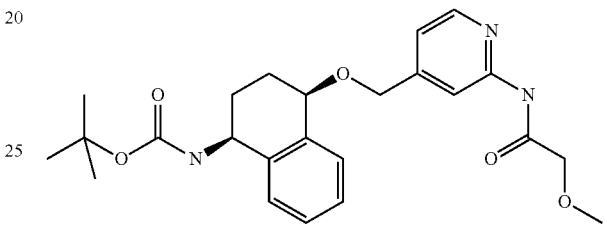

Intermediate 9b (1.37 g, 3.70 mmol) was dissolved in DCM (25 mL) under argon and cooled in an ice bath. To this mixture was added DIPEA (0.96 mL, 6.00 mmol), then methoxyacetyl chloride (0.36 mL, 4.00 mmol). The mixture was stirred with cooling for 15 min, then diluted with saturated sodium hydrogen carbonate solution, and stirred at room temperature for 5 min. The phases were separated, and organic layer dried (Na$_2$SO$_4$) and evaporated. Purification by FCC, eluting with 0-100% ethyl acetate in cyclohexane, gave the title compound (626 mg, 38%). LCMS (Method 3): Rt 3.85 min, m/z 464.2 [MNa$^+$].

d. N-[4-((1R,4S)-4-Amino-1,2,3,4-tetrahydro-naphthalen-1-yloxymethyl)-pyridin-2-yl]-2-methoxyacetamide (Intermediate 9d)

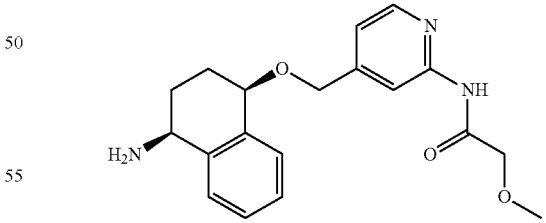

To a solution of Intermediate 9c (0.62 g, 1.41 mmol) in DCM (7 mL), trifluoroacetic acid (1 mL) was added, and the mixture stirred at RT for 3 h. The solution was purified on SCX-2 cartridge, washing with MeOH then eluting with 0.4-1M NH$_3$ in MeOH, to give the impure title compound (0.42 g). Additional purification by FCC, eluting with 0-14% [2M NH$_3$ in MeOH] in DCM, gave the title compound as a colourless gum (0.28 g, 58%). LCMS (Method 3): Rt 0.44 and 2.06 min, m/z 364 [MNa$^+$].

e. N-(4-{(1R,4S)-4-[3-(5-tert-Butyl-2-p-tolyl-2H-pyrazol-3-yl)-ureido]-1,2,3,4-tetrahydro-naphthalen-1-yloxymethyl}-pyridin-2-yl)-2-methoxy-acetamide (Example 9)

To a solution of Intermediate 9d (277 mg, 0.81 mmol) in 1,4-dioxane (10 mL), (5-tert-butyl-2-p-tolyl-2H-pyrazol-3-yl)-carbamic acid 2,2,2-trichloro-ethyl ester (Synthetic Communications, 39(22), 3999-4009; 2009; 394 mg, 0.97 mmol) and DIPEA (0.21 mL, 1.30 mmol) were added. The mixture was heated at 80° C. under argon for 16 h, then evaporated to dryness. The residue was purified by FCC, eluting with 0-100% ethyl acetate in cyclohexane, to give the slightly impure title compound (378 mg). This was further purified by preparative HPLC (Method 6) to give the title compound as a white solid (305 mg, 63%). LCMS (Method 5): Rt 5.09 min, m/z 597.2 [MH$^+$] $^1$H NMR (400 MHz, d$_6$-DMSO): 1.21 (9H, s), 1.76-1.87 (2H, m), 1.90-2.01 (2H, m), 2.31 (3H, s), 3.31 (3H, s), 4.00 (2H, s), 4.43-4.50 (1H, m), 4.57-4.76 (3H, m), 4.75-4.83 (1H, m), 6.27 (1H, s), 7.03 (1H, d, J 8.7 Hz), 7.06 (1H, dd, J 5.2, 1.4 Hz), 7.15-7.32 (7H, m), 7.36-7.40 (1H, m), 7.93 (1H, s), 8.08 (1H, s), 8.22 (1H, d, J 5.2 Hz), 9.88 (1H, br s).

Example 10

1-(5-tert-Butyl-2-p-tolyl-2H-pyrazol-3-yl)-3-{(1S,4R)-4-[3-(2-hydroxy-ethylsulfanyl)-phenyl]-[1,2,4]triazolo[4,3-a]pyridin-6-yloxy)-1,2,3,4-tetrahydro-naphthalen-1-yl-urea

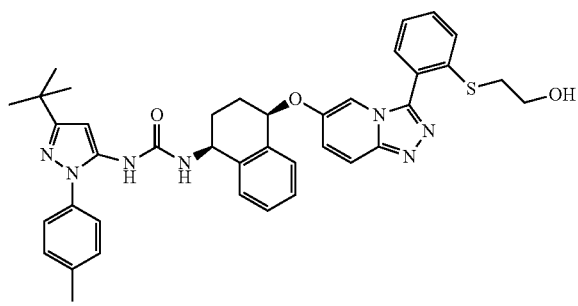 [SMILES: Cc1ccc(-n2nc(C(C)(C)C)cc2NC(=O)N[C@H]2CC[C@@H](Oc3ccc4nnc(-c5ccccc5SCCO)n4c3)c3ccccc32)cc1]

a. 2-{2-[5-fluoro-pyridin-2-yl)-hydrazonomethyl]-phenylsulfanyl}-ethanol (Intermediate 10a)

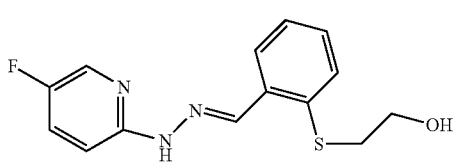 [SMILES: OCCSc1ccccc1/C=N/Nc1ccc(F)cn1]

The title compound was prepared starting from 5-fluoro-2-hydrazinyl-pyridine (for reference procedure see WO2010022076) and 2-(2-hydroxy-ethylsulfanyl)-benzaldehyde (for reference procedure see WO2009098612) with a similar procedure to that described in Example 4 step a. LCMS (Method 1): Rt 2.93 min, m/z 292 [MH$^+$].

b. 2-[2-(6-Fluoro-[1,2,4]triazolo[4,3-a]pyridin-3-yl)-phenylsulfanyl]-ethanol (Intermediate 10b)

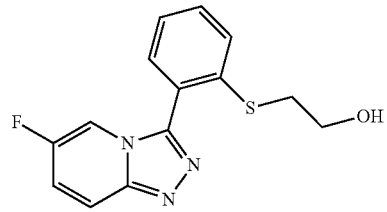 [SMILES: OCCSc1ccccc1-c1nnc2ccc(F)cn12]

The title compound was prepared starting from Intermediate 10a and (diacetoxyiodo)benzene with a similar procedure to that described Example 4 step b. LCMS (Method 1): Rt 2.33 min, m/z 290 [MH$^+$].

c. 6-Fluoro-3-[2-(2-triisopropylsilanyloxy-ethylsulfanyl)-phenyl]-[1,2,4]triazolo[4,3-a]pyridine (Intermediate 10c)

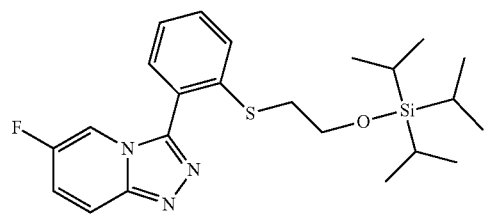 [SMILES: CC(C)[Si](OCCSc1ccccc1-c1nnc2ccc(F)cn12)(C(C)C)C(C)C]

Triisopropylsilyl chloride (3.30 g, 17.1 mmol) was added to a solution of Intermediate 10b (3.30 g, 11.4 mmol), imidazole (0.93 g, 13.7 mmol) and DMAP (139 mg, 1.14 mmol) in THF (35 mL) and the mixture heated at 50° C. overnight. The cooled mixture was washed with HCl (1M, 15 mL). The aqueous phase was extracted with 2-methyl tetrahydrofuran (2×100 mL). The combined organic extracts were washed with brine and dried (MgSO$_4$). The solvent was evaporated and the residue purified by FCC, using 25-80% cyclohexane in EtOAc, to afford the title compound as a brown oil (3.45 g, 68%). LCMS (Method 2): Rt 4.78 min, m/z 446 [MH$^+$].

d. (1S,4R)-4-{3-[2(2-Triisopropylsilanyloxy-ethylsulfanyl)-phenyl]-[1,2,4]triazolo[4,3-a]pyridin-6-yloxy}-1,2,3,4-tetrahydro-naphthalen-1-ylamine (Intermediate 10d)

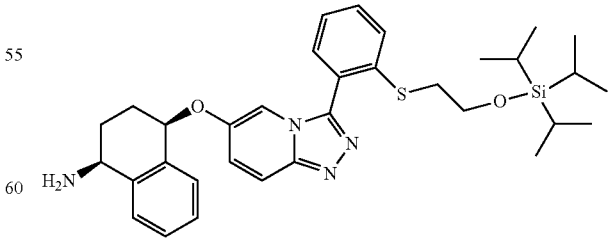

The title compound was prepared starting from Intermediate 10c and Intermediate 1d with a similar procedure to that described in Example 1 step g. LCMS (Method 1): Rt 3.02 min, m/z 589 [MH$^+$].

e. 1-(5-tert-Butyl-2-p-tolyl-2H-pyrazol-3-yl)-3-[(1S, 4R)-4-{3-[2-(2-triisopropylsilanyloxy-ethylsulfanyl)-phenyl]-[1,2,4]triazolo[4,3-a]pyridin-6-yloxy)-1,2,3,4-tetrahydro-naphthalen-1-yl]urea (Intermediate 10e)

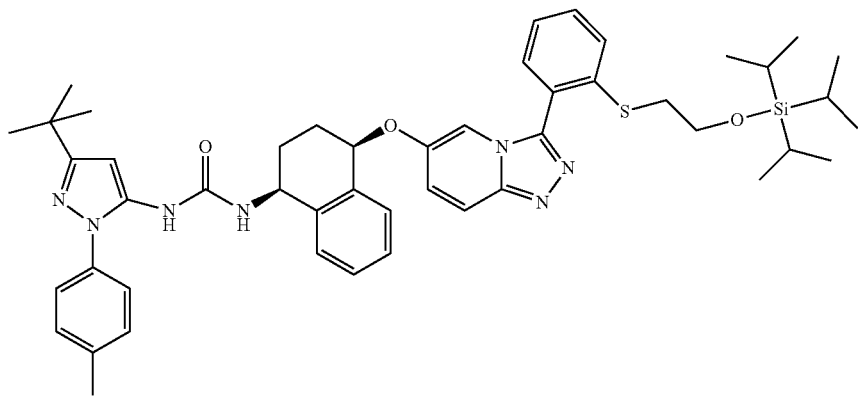 [SMILES: Cc1ccc(-n2nc(C(C)(C)C)cc2NC(=O)N[C@H]2CC[C@@H](Oc3ccc4nnc(-c5ccccc5SCCO[Si](C(C)C)(C(C)C)C(C)C)n4c3)c3ccccc32)cc1]

The title compound was prepared starting from Intermediate 10d and [5-tert-butyl-2-p-tolyl-2H-pyrazol-3-yl]-carbamic acid 2,2,2-trichloro-ethyl ester (Synthetic Communications, 39(22), 3999-4009; 2009) with a similar procedure to that described in Example 1 step h. LCMS (Method 4): Rt 4.29 min, m/z 844 [MH+].

f. 1-(5-tert-butyl-2-p-tolyl-2H-pyrazol-3-yl)-3-{(1S,4R)-4-[3-(2-hydroxy-ethylsulfanyl)-phenyl]-[1,2,4]triazolo[4,3-a]pyridin-6-yloxy)-1,2,3,4-tetrahydro-naphthalen-1-yl-urea (Example 10)

Triethylamine trihydrofluoride (163 mg, 1.01 mmol) was added portionwise to a solution of Intermediate 10e (428 mg, 0.51 mmol) and THF (3.0 mL) at 0° C. The ice-bath was removed and the mixture stirred overnight at RT. Saturated aqueous NaHCO$_3$ (10 mL) was added to the mixture which was then extracted with ethyl acetate (3×10 mL). The combined organic extracts were washed with brine (15 mL) and dried (Na$_2$SO$_4$). The solvent was evaporated and the residue purified by HPLC (eluting with 50-95% MeCN in H$_2$O, (0.1% HCO$_2$H)) to give the title compound as a colourless powder (8.0 mg, 2.2%). LCMS (Method 5): Rt 4.72 mins, m/z=688 [MH+]. $^1$H NMR (400 MHz, CDCl$_3$): 1.32 (9H, s), 1.81-2.07 (3H, m), 2.16-2.23 (1H, m), 2.36 (3H, s), 2.90 (2H, t), 3.59 (2H, t), 5.02 (1H, m), 5.11 (1H, m), 5.25 (1H, m), 6.25 (1H, s), 6.30 (1H br s), 7.12 (1H, m), 7.19-7.38 (10H, m), 7.44-7.57 (3H, m), 7.69-7.73 (2H, m).

Example 11

1-{5-tert-Butyl-2-[3-(2-dimethylamino-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea

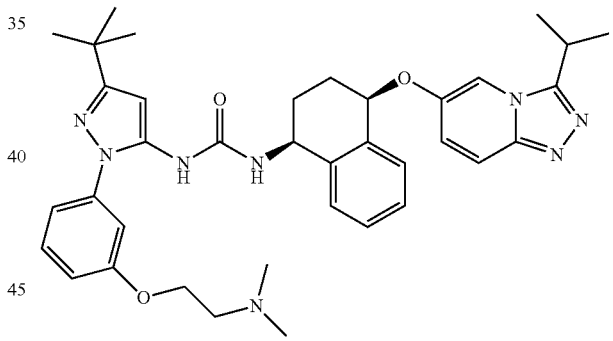

a. 5-tert-Butyl-2-(3-methoxy-phenyl)-2H-pyrazol-3-ylamine (Intermediate 11a)

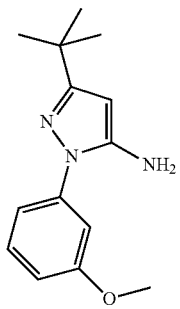 [SMILES: COc1cccc(-n2nc(C(C)(C)C)cc2N)c1]

3-Methoxylphenylhydrazine hydrochloride salt (5.00 g, 28.6 mmol) and 4,4-dimethyl-3-oxopentanenitrile (3.94 g, 31.5 mmol) were heated to 100° C. in MeOH for 18 h. The reaction was cooled and evaporated in vacuo. The residue was taken up in EtOAc (200 mL) and water (200 mL) and the aqueous layer extracted with EtOAc (3×). The combined organic layers were washed with brine, dried (MgSO$_4$), filtered and evaporated in vacuo. Purification by FCC, using 0-50% EtOAc in cyclohexane, gave the title compound (5.03 g) as a mixture with 4,4-dimethyl-3-oxopentanenitrile. This was used in the next reaction without further purification. $^1$H NMR (400 MHz, d$_6$-DMSO): 1.21 (9H, s), 3.79 (3H, s), 5.20 (2H, br s), 5.37 (1H, s), 6.82-6.85 (1H, dd, J 8.3, 2.2 Hz), 7.12-7.17 (2H, m), 7.32-7.36 (1H, t, J 8.1 Hz).

b. 3-(5-Amino-3-tert-butyl-pyrazol-1-yl)-phenol (Intermediate 11b)

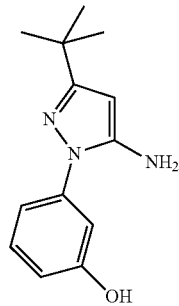 [SMILES: CC(C)(C)c1cc(N)n(-c2cccc(O)c2)n1]

Aluminium chloride (13.6 g, 102.6 mmol) was added portionwise to a solution of Intermediate 11a (5.03 g) in DCM (50.0 mL) and the reaction heated to 45° C. for 18 h. Additional aluminium chloride (4.00 g, 30.0 mmol) was added and the reaction heated to 45° C. for a further 18 h. The mixture was cooled and slowly transferred into ice cold water, then extracted into EtOAc (3×). The combined organic layers were washed with brine, dried (MgSO$_4$), filtered and evaporated in vacuo. Purification by FCC, using 0-50% EtOAc in cyclohexane, gave the title compound (2.40 g, 10.4 mmol, 36%). LCMS (Method 1): Rt 2.03 mins, m/z 232 [MH$^+$].

c. 5-tert-Butyl-2-[3-(2-dimethylamino-ethoxy)-phenyl]-2H-pyrazol-3-ylamine (Intermediate 11c)

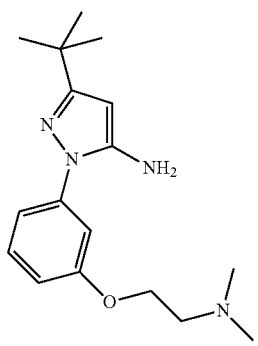 [SMILES: CN(C)CCOc1cccc(-n2nc(C(C)(C)C)cc2N)c1]

DIAD (847 μL, 4.32 mmol) was added slowly to a solution of Intermediate 11b (500 mg, 2.16 mmol), 2-dim- ethylaminoethanol (326 μL, 3.25 mmol) and triphenylphosphine (1.13 g, 4.32 mmol) in THF (10 mL) and the reaction stirred for 72 h. The reaction mixture was partitioned between EtOAc (75 mL) and H$_2$O (75 mL) and the aqueous layer extracted with EtOAc (3×). The combined organic layers were washed with brine, dried (MgSO$_4$), filtered and evaporated in vacuo. Purification by FCC, using 0.5-6% [2M NH$_3$ in MeOH] in DCM, gave the title compound (472 mg, 1.56 mmol, 72%). LCMS (Method 4): Rt 0.32 min, m/z 303 [MH$^+$].

d. {5-tert-Butyl-2-[3-(2-dimethylamino-ethoxy)-phenyl]-2H-pyrazol-3-yl}-carbamic acid 2,2,2-trichloro-ethyl ester (Intermediate 11d)

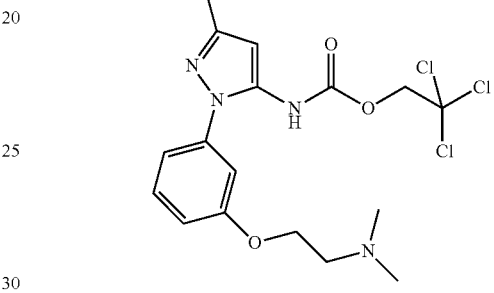

Intermediate 11c (100 mg, 0.33 mol) was dissolved in THF (3.0 mL) and DIPEA (115 μL, 0.66 mmol) was added followed by 2,2,2-trichloroethylchloroformate (68 μL, 0.50 mmol). The reaction was stirred for 60 min and then partitioned between EtOAc (50 mL) and H$_2$O (50 mL) and the aqueous layer extracted with EtOAc (3×). The combined organic layers were washed with brine, dried (MgSO$_4$), filtered and evaporated in vacuo to yield the title compound (130 mg), contaminated with bis-acylated material. This was used in the next step without further purification. LCMS (Method 2): Rt 2.95 min, m/z 475, 479 [M-H$^-$].

e. 1-{5-tert-Butyl-2-[3-(2-dimethylamino-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]urea (Example 11)

Diisopropylethylamine (81 μL, 0.30 mmol) was added to a solution of Intermediate 1g (105 mg, 0.32 mmol) and Intermediate 11d (122 mg) in 1,4-dioxane (3.0 mL). The reaction was heated to 100° C. for 18 h. After cooling, the mixture was partitioned between EtOAc (50 mL) and water (50 mL). The aqueous layer was extracted into EtOAc (3×) and the combined organic layers were washed with brine, dried (MgSO$_4$) and concentrated in vacuo. Purification by FCC, using 0-10% [2M NM$_3$ in MeOH] in DCM, gave crude product. Further purification by HPLC (C18 X-select column, 10-98% MeCN in H$_2$O, 0.1% formic acid) afforded the title compound (22 mg, 0.033 mmol, 11%). LCMS (Method 5): Rt 3.40 mins, m/z 651 [MH$^+$]. $^1$H NMR (400 MHz, CDCl$_3$): 1.31 (9H, s), 1.43-1.46 (3H, d, J 6.8 Hz), 1.46-1.49 (3H, d, J 6.8 Hz), 1.90-2.20 (4H, m), 2.43 (6H, s), 2.89-2.95 (1H, dd, J 13.3, 5.2 Hz), 2.95-3.01 (1H, dd, J 13.3, 5.2 Hz), 3.20-3.30 (1H, sp, J 6.8 Hz), 4.23-4.28 (2H, t, J 5.2 Hz), 5.04-5.11 (1H, td, J 8.8, 5.6 Hz), 5.14-5.18 (1H, t, J 4.2 Hz), 6.42 (1H, s), 6.42-6.48 (1H, br s), 6.81-6.85 (1H, dd, J 8.3, 1.9 Hz), 6.98-7.00 (1H, t, J 4.3 Hz), 7.00-7.04 (1H, dd, J 9.9, 1.9 Hz), 7.12-7.16 (1H, m), 7.22-7.34 (5H, m), 7.43-7.44 (1H, d, J 1.7 Hz), 7.61-7.65 (1H, d, J 9.7 Hz).

The following examples were prepared starting from suitable starting materials and using, as appropriate, analogous procedures to those indicated.

| Example No. | Starting Material/Intermediate used (Ref) | Methods used | Example Structure | NMR (400 MHz) δ | LCMS |
|---|---|---|---|---|---|
| 12 | ![structure with NH2, Cl, OH, tert-butyl pyrazole] (WO2007091152) | Example 6 step b & Example 1 step h | 1-[5-tert-Butyl-2-(3-chloro-4-hydroxy-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea | (d₆-DMSO): 1.21 (9H, s), 1.34 (6H, m), 1.78-1.92 (2H, m), 1.99-2.10 (2H, m), 3.49-3.56 (1H, m), 4.74-4.81 (1H, m), 5.49 (1H, t, J 4.3 Hz), 6.24 (1H, s), 7.01-7.05 (2H, m), 7.12 (1H, dd, J 2.0, 9.8 Hz), 7.19-7.36 (5H, m), 7.39 (1H, d, J 2.6 Hz), 7.64 (1H, d, J 9.5 Hz), 7.96 (1H, s), 8.16 (1H, m), 10.53 (1H, br s) | (Method 5): Rt 4.31 mins, m/z 614 [MH⁺]. |
| 13 | Intermediate 1 g | Example 2 step d | 1-Cyclopropyl-3-[(1S,4R)-4-(3-isopropyl-[1,2,4]triazolo[4,3-a]pyridin-6-yloxy)-1,2,3,4-tetrahydro-naphthalen-1-yl]-urea | (d₆-DMSO): 0.35-0.40 (2H, m), 0.57- 0.62 (2H, m), 1.39 (6H, t, J 7.2 Hz), 1.85-1.92 (2H, m), 1.99-2.09 (1H, m), 2.12-2.21 (1H, m), 2.48 (1H, m obs), 3.53-3.63 (1H, m), 4.80-4.86 (1H, m), 5.53 (1H, t, J 4.0 Hz), 6.12 (1H, m), 6.29 (1H, d, J 9.0 Hz), 7.17 (1H, dd, J 2.0 9.8 Hz), 7.24-7.30 (1H, m), 7.33- 7.39 (3H, m), 7.68 (1H, d, J 9.8 Hz), 8.20 (1H, m). | (Method 5): Rt 3.16 mins. m/z 406 [MH⁺]. |

| Example No. | Starting Material/Intermediate used (Ref) | Methods used | Example Structure | NMR (400 MHz) δ | LCMS |
|---|---|---|---|---|---|
| 14 | 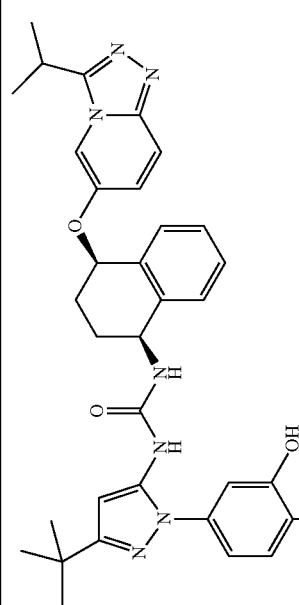 (WO2007091152) | Example 6 step b & Example 1 step h | 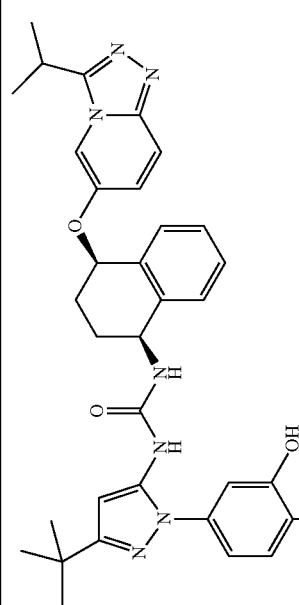 1-(5-tert-Butyl-2-(4-chloro-3-hydroxyphenyl)-2H-pyrazol-3-yl)-3-[(1S,4R)-4-(3-isopropyl-[1,2,4]triazolo[4,3-a]pyridin-6-yloxy)-1,2,3,4-tetrahydronaphthalen-1-yl]-urea | (d$_6$DMSO): 1.22 (9H, s), 1.32-1.35 (6H, dd, J 5.6 Hz), 1.77-1.93 (2H, m), 2.01-2.10 (2H, m), 3.49-3.56 (1H, m), 4.75-4.81 (1H, m), 5.49 (1H, t, J 4.5 Hz), 6.28 (1H, s), 6.88-6.91 (1H, m), 7.04-7.13 (3H, m), 7.22-7.40 (5H, m), 7.63-7.65 (1H, d, J 10.02 Hz), 8.08 (1H, s), 8.16 (1H, s, J 1.63 Hz) | (Method 5): Rt 4.34 mins, m/z 614/616 |
| 15 | 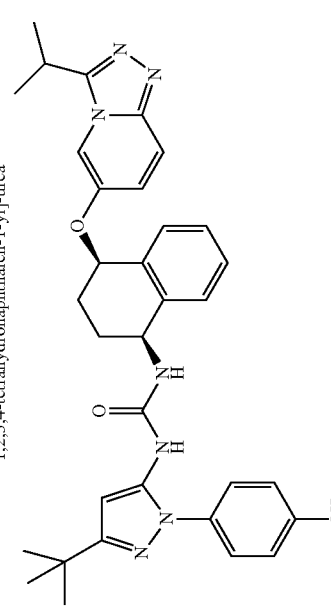 (WO2007091336) | Example 6 step b & Example 1 step h | 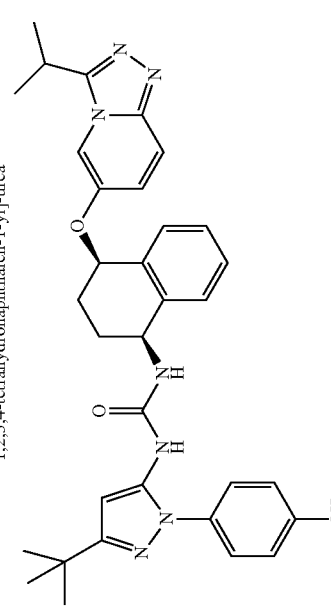 1-[5-tert-Butyl-2-(4-hydroxy-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea | (300 MHz, d$_6$-DMSO): 1.26 (9H, s), 1.38 (6H, dd, J 4.3, 7.0 Hz), 1.82-1.98 (2H, m), 2.06-2.13 (2H, m), 3.53-3.62 (1H, m), 4.79-4.87 (1H, m), 5.54 (1H, t, J 4.0 Hz), 6.29 (1H, s), 6.84-6.89 (2H, m), 7.09-7.41 (8H, m), 7.69 (1H, d, J 10 Hz), 7.94 (1H, s), 8.21 (1H, m), 9.75 (1H, s). | (Method 5): Rt 4.06 mins, m/z 580 [MH$^+$]. |

| Example No. | Starting Material/Intermediate used (Ref) | Methods used | Example Structure | NMR (400 MHz) δ | LCMS |
|---|---|---|---|---|---|
| 16 | 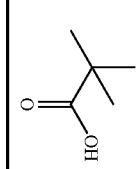 | Example 1 steps e to h | 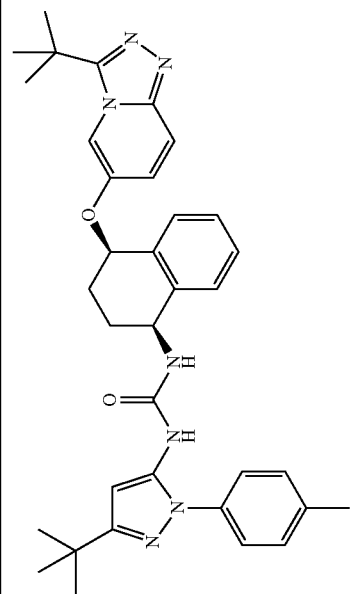

1-(5-tert-Butyl-2-p-tolyl-2H-pyrazol-3-yl)-3-[(1S,4R)-4-(3-tert-butyl-[1,2,4]triazolo[4,3-a]pyridin-6-yloxy)-1,2,3,4-tetrahydro-naphthalen-1-yl]-urea | (CDCl$_3$): 1.30 (9H, s), 1.52 (9H, s), 1.84-1.94 (1H, m), 2.00-2.10 (2H, m), 2.18-2.28 (1H, m), 2.35 (3H, s), 5.01-5.08 (1H, td, J 9.3, 5.4 Hz), 5.11-5.16 (1H, t, J 3.8 Hz), 5.21-5.26 (1H, d, J 8.9 Hz), 6.23 (1H, s), 6.32 (1H, s), 7.01-7.05 (1H, dd, J 9.7, 1.9 Hz), 7.18-7.22 (3H, m), 7.23-7.29 (3H, m), 7.35-7.38 (2H, d, J 8.4 Hz), 7.61-7.65 (1H, d, J 9.9 Hz), 7.67-7.70 (1H, d, J 1.8 Hz) | (Method 5) Rt 4.83 mins, m/z 592.2 [MH$^+$]. |
| 17 | Intermediate 1g & 5-tert-butyl-isoxazol-3-ylamine | Example 8 | 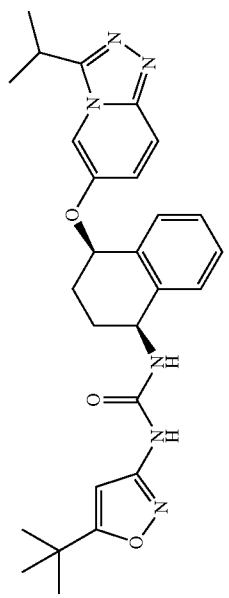

1-(5-tert-Butyl-isoxazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea | (CDCl$_3$): 1.29 (9H, s), 1.43-1.46 (3H, d, J 6.9 Hz), 1.47-1.50 (3H, d, J 6.9 Hz), 2.08-2.22 (3H, m), 2.28-2.36 (1H, m), 3.20-3.32 (1H, sp, J 6.9 Hz), 5.12-5.24 (2H, m), 5.80 (1H, s), 7.09-7.13 (1H, dd, J 9.8, 1.9 Hz), 7.23-7.27 (2H, m), 7.30-7.36 (1H, m), 7.43-7.46 (1H, d, J 1.9 Hz), 7.47-7.51 (1H, d, J 7.9 Hz), 7.66-7.69 (1H, d, J 9.8 Hz), 7.76-7.82 (1H, br d, J 7.5 Hz), 7.88 (1H, br s) | (Method 5) Rt 4.27 mins, m/z 489.2 [MH$^+$] |

| Example No. | Starting Material/Intermediate used (Ref) | Methods used | Example Structure | NMR (400 MHz) δ | LCMS |
|---|---|---|---|---|---|
| 18 | 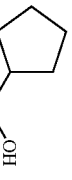 | Example 1 steps e to h | 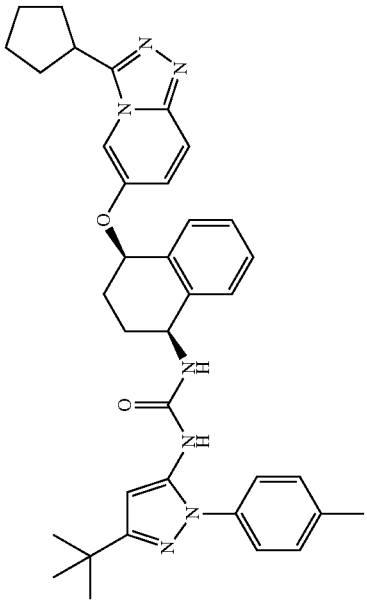  1-(5-tert-Butyl-2-p-tolyl-2H-pyrazol-3-yl)-3-[(1S,4R)-4-(3-cyclopentyl-[1,2,4]triazolo[4,3-a]pyridin-6-yloxy)-1,2,3,4-tetrahydro-naphthalen-1-yl]-urea | (CDCl₃): 1.29 (9H, s), 1.66-1.76 (2H, m), 1.78-1.94 (3H, m), 1.98-2.14 (6H, m), 2.18-2.26 (1H, m), 2.34 (3H, s), 3.25-3.34 (1H, qn, J 6.9 Hz), 5.02-5.10 (1H, td, J 8.9, 5.2 Hz), 5.14-5.17 (1H, t, J 3.9 Hz), 5.25-5.30 (1H, d, J 8.9 Hz), 6.24 (1H, s), 6.34 (1H, s), 6.98-7.02 (1H, dd, J 9.9, 2.1 Hz), 7.17-7.21 (3H, m), 7.23-7.29 (3H, m), 7.34-7.38 (1H, d, J 8.3 Hz), 7.40-7.41 (1H, d, J 1.9 Hz), 7.55-7.59 (1H, d, J 9.9 Hz) | (Method 5) Rt 4.85 mins, m/z 604.2 [MH⁺]. |
| 19 | 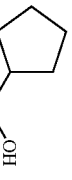  (WO2007091152) | Example 6 step b & Example 1 step h | 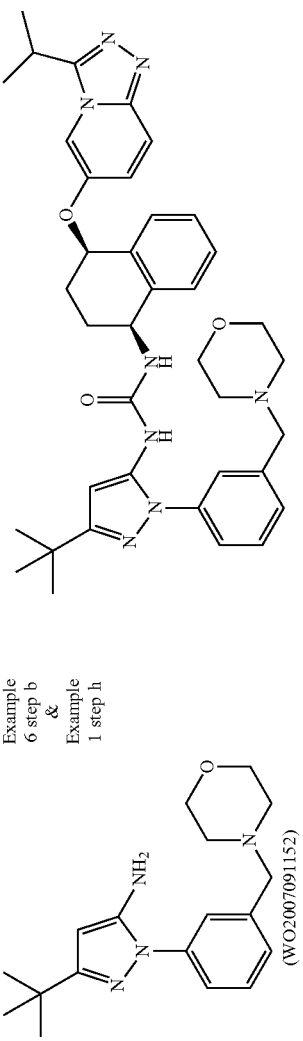  1-[5-tert-Butyl-2-(3-morpholin-4-ylmethyl-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea, formic acid salt | (d₆-DMSO): 1.22 (9H, s), 1.30-1.32 (3H, d, J 6.8 Hz), 1.32-1.35 (3H, d, J 6.8 Hz), 1.77-1.93 (2H, m), 2.00-2.09 (2H, m), 2.29-2.35 (4H, m), 3.46 (2H, s), 3.48-3.52 (4H, m), 3.49-3.55 (1H, sp, J 6.8 Hz), 4.74-4.82 (1H, td, J 8.7, 5.2 Hz), 5.45-5.50 (1H, t, J 4.33 Hz), 6.28 (1H, s), 6.98-7.02 (1H, d, J 8.5 Hz), 7.09-7.13 (1H, dd, J 10.0, 2.2 Hz), 7.20-7.31 (4H, m), 7.32-7.43 (4H, m), 7.61-7.64 (1H, d, J 9.9 Hz), 8.04 (1H, s), 8.11 (1H, s), 8.14-8.16 (1H, d, J 1.7 Hz) | (Method 5) Rt 3.34 mins, m/z 663.2 [MH⁺]. |

| Example No. | Starting Material/Intermediate used (Ref) | Methods used | Example Structure | NMR (400 MHz) δ | LCMS |
|---|---|---|---|---|---|
| 20 | 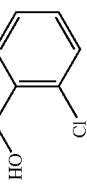 | Example 1 steps e to h | 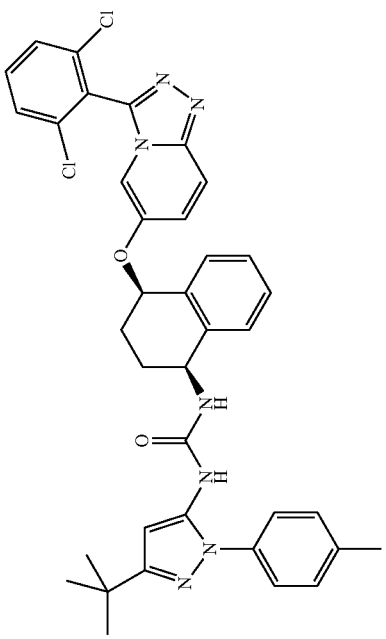<br>1-(5-tert-Butyl-2-p-tolyl-2H-pyrazol-3-yl)-3-{(1S,4R)-4-(3-(2,6-dichloro-phenyl)-[1,2,4]triazolo[4,3-a]pyridin-6-yloxy)-1,2,3,4-tetrahydro-naphthalen-1-yl}-urea | (CDCl$_3$): 1.32 (9H, s), 1.83-1.89 (1H, m), 1.95-2.07 (2H, m), 2.17-2.23 (1H, m), 2.38 (3H, s), 5.00-5.09 (2H, m), 5.11-5.13 (1H, m), 6.15 (1H, s), 6.24 (1H, s), 7.15 (1H, dd, J 2.29, 7.64 Hz), 7.18-7.21 (2H, m), 7.23 (1H, m), 7.25-7.29 (4H, m), 7.37-7.39 (2H, m), 7.46-7.55 (3H, m), 7.79 (1H, dd, J 0.88, 8.83 Hz) | (Method 5) Rt 5.20 mins, m/z 680-684 [MH$^+$]. |
| 21 | 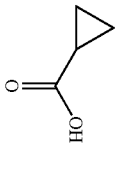 | Example 1 steps e to h | 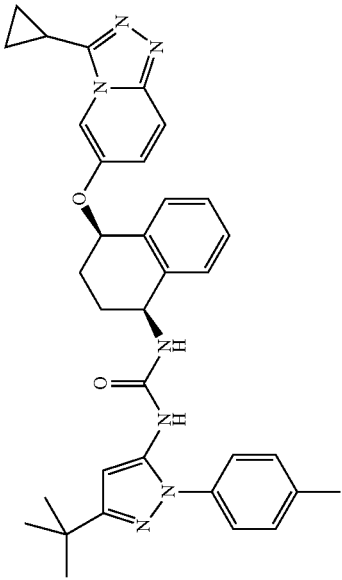<br>1-(5-tert-Butyl-2-p-tolyl-2H-pyrazol-3-yl)-3-[(1S,4R)-4-(3-cyclopropyl-[1,2,4]triazolo[4,3-a]pyridin-6-yloxy)-1,2,3,4-tetrahydro-naphthalen-1-yl]-urea | (CDCl$_3$): 1.13-1.17 (4H, m), 1.33 (9H, s), 1.90-1.98 (2H, m), 2.05-2.13 (2H, m), 2.24-2.30 (1H, m), 2.38 (3H, s), 5.06-5.12 (1H, m), 5.21-5.25 (1H, m), 6.26 (1H, s), 6.29 (1H, br s), 7.05 (1H, dd, J 2.28, 9.83 Hz), 7.22-7.24 (3H, m), 7.31 (3H, m), 7.40 (2H, d, J 8.24 Hz), 7.60-7.63 (2H, m). | (Method 5) Rt 4.57 mins, m/z 576 [MH$^+$]. |

| Example No. | Starting Material/Intermediate used (Ref) | Methods used | Example Structure | NMR (400 MHz) δ | LCMS |
|---|---|---|---|---|---|
| 22 | pyridine-2-carboxylic acid | Example 1 steps e to h | 1-(5-tert-Butyl-2-p-tolyl-2H-pyrazol-3-yl)-3-{(1S,4R)-4-(3-pyridin-2-yl-[1,2,4]triazolo[4,3-a]pyridin-6-yloxy)-1,2,3,4-tetrahydro-naphthalen-1-yl}-urea | (CDCl₃): 1.33 (9H, s), 1.90-2.00 (2H, m), 2.05-2.17 (2H, m), 2.34 (3H, s), 2.32-2.40 (1H, m), 5.12 (1H, t, J 6.90 Hz), 5.35 (2H, m), 6.28 (1H, s), 6.32 (1H, br s), 7.12 (1H, dd, J 2.18, 9.68 Hz), 7.17-7.19 (2H, m), 7.32-7.41 (4H, m), 7.71 (1H, dd, J 0.81, 9.83, Hz), 7.84 (1H, td, J 1.80 7.82, Hz), 8.45 (1H, d, J 8.07 Hz), 8.64 (1H, ddd, J 0.94, 1.78, 4.92, Hz), 9.55 (1H, d, J 2.20 Hz). | (Method 5) Rt 5.11 mins, m/z 613 [MH⁺]. |
| 23 | 2-chlorobenzoic acid | Example 1 steps e to h | 1-(5-tert-Butyl-2-p-tolyl-2H-pyrazol-3-yl)-3-{(1S,4R)-4-(3-(2-chloro-phenyl)-[1,2,4]triazolo[4,3-a]pyridin-6-yloxy)-1,2,3,4-tetrahydro-naphthalen-1-yl}-urea | (CDCl₃): 1.32 (9H, s), 1.84-1.89 (1H, m), 1.96-2.07 (2H, m), 2.19-2.25 (1H, m), 2.37 (3H, s), 5.01-5.07 (1H, m), 5.11-5.14 (2H, m), 6.24 (1H, s), 6.25 (1H, s), 7.13 (1H, dd, J 2.18, 10.15 Hz), 7.18-7.30 (4H, m), 7.36-7.39 (2H, m), 7.46-7.60 (3H, m), 7.67-7.69 (1H, dd, J 1.72, 7.51 Hz), 7.74-7.77 (1H, d, J 9.37 Hz) | (Method 5) Rt 5.11 mins, m/z 646 & 648 [MH⁺]. |

| Example No. | Starting Material/Intermediate used (Ref) | Methods used | Example Structure | NMR (400 MHz) δ | LCMS |
|---|---|---|---|---|---|
| 24 | 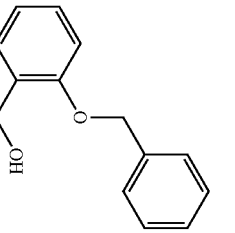 | Example 1 steps e to h | 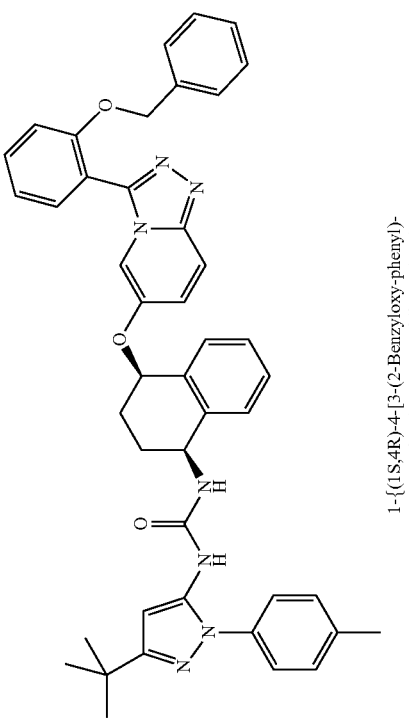<br>1-{(1S,4R)-4-[3-(2-Benzyloxy-phenyl)-[1,2,4]triazolo[4,3-a]pyridin-6-yloxy]-1,2,3,4-tetrahydro-naphthalen-1-yl}-3-(5-tert-butyl-2-p-tolyl-2H-pyrazol-3-yl)-urea | (CDCl₃): 1.32 (9H, s), 1.67-1.96 (3H, m), 2.36 (3H, s), 4.89 (1H, m), 4.95-5.00 (1H, m), 5.06 (1H, s), 5.08 (2H, s), 6.18 (1H, s), 6.24 (1H, s), 7.10-7.06 (4H, m), 7.14-7.27 (9H, m), 7.36-7.38 (2H, m), 7.48 (1H, d, J 1.71 Hz), 7.51-7.56 (1H, m), 7.69 (1H, d, J 9.36 Hz), 7.75 (1H, dd, J 1.69, 7.46 Hz) | (Method 5): Rt 5.34 mins, m/z 718 [MH⁺]. |
| 25 | Intermediate 2c & 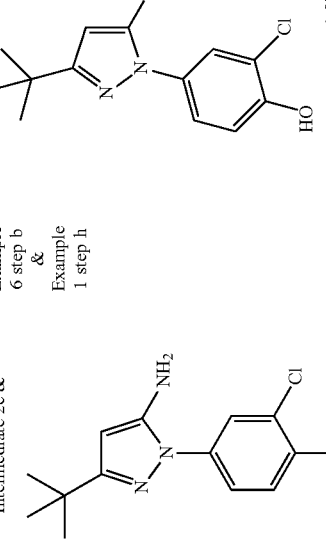 (WO2007091152) | Example 6 step b & Example 1 step h | (structure shown)<br>1-[5-tert-Butyl-2-(3-chloro-4-hydroxy-phenyl)-2H-pyrazol-3-yl]-3-{(1S,4S)-4-(3-isopropyl-[1,2,4]triazolo[4,3-a]pyridin-6-yloxy)-1,2,3,4-tetrahydro-naphthalen-1-yl}-urea | (d₆-DMSO): 1.25 (9H, s), 1.37 (3H, d), 1.39 (3H, d), 1.75 (1H, m), 2.01 (1H, m), 2.14 (2H, m), 3.57 (1H, sept), 4.90 (1H, m), 5.57 (1H, m), 6.28 (1H, s), 6.99 (1H, d), 7.05 (1H, d), 7.21-7.42 (7H, m), 7.68 (1H, s), 7.93 (1H, s), 8.21 (1H, m), 10.51 (1H, br s). | (Method 5): Rt 4.27 mins, m/z 614 [MH⁺]. |

| Example No. | Starting Material/Intermediate used (Ref) | Methods used | Example Structure | NMR (400 MHz) δ | LCMS |
|---|---|---|---|---|---|
| 26 | 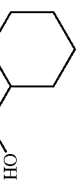 | Example 1 steps e to h | 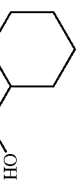

1-(5-tert-Butyl-2-p-tolyl-2H-pyrazol-3-yl)-3-[(1S,4R)-4-(3-cyclohexyl-[1,2,4]triazolo[4,3-a]pyridin-6-yloxy)-1,2,3,4-tetrahydro-naphthalen-1-yl]-urea | (CDCl$_3$): 1.29 (9H, s), 1.33-1.45 (2H, m), 1.71-1.79 (4H, m), 1.86-1.91 (3H, m), 1.92-1.96 (1H, m), 1.98-2.10 (4H, m), 2.19-2.25 (1H, m), 2.33 (3H, s), 2.85 (1H, tt, J 11.6, 3.5 Hz), 5.06 (1H, td, J 9.0, 5.3 Hz), 5.18 (1H, t, J 3.8 Hz), 5.33 (1H, d, J 8.5 Hz), 6.24 (1H, s), 6.39 (1H, s), 6.99 (1H, dd, J 9.9, 1.9 Hz), 7.19 (2H, d, J 8.2 Hz), 7.21-7.29 (3H, m), 7.36 (2H, d, J 8.3 Hz), 7.39 (1H, d, J 1.5 Hz), 7.51 (1H, d, J 9.9 Hz) | (Method 5): Rt 4.95 mins, m/z 618.2 [MH$^+$]. |
| 27 | Intermediate 2c & 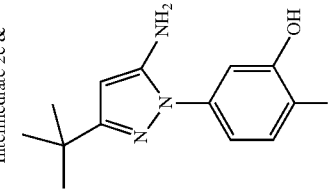
(WO2007091152) | Example 6 step b & Example 1 step h | 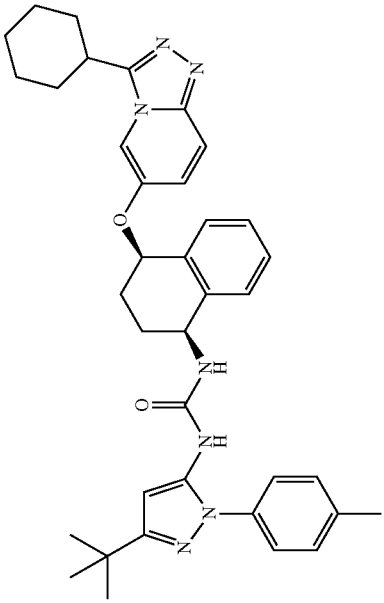

1-[5-tert-Butyl-2-(4-chloro-3-hydroxy-phenyl)-2H-pyrazol-3-yl]-3-[(1S,4S)-4-(3-isopropyl-[1,2,4]triazolo[4,3-a]pyridin-6-yloxy)-1,2,3,4-tetrahydro-naphthalen-1-yl]-urea | (d$_6$-DMSO): 1.26 (9H, s), 1.37 (3H, d), 1.39 (3H, d), 1.75 (1H, m), 2.02 (1H, m), 2.11-2.19 (2H, m), 3.57 (1H, sept), 4.91 (1H, m), 5.57 (1H, dd), 6.33 (1H, s), 6.92 (1H, dd), 7.01 (1H, d), 7.10 (1H, d), 7.23 (1H, dd), 7.28-7.43 (5H, m), 7.69 (1H, d), 8.05 (1H, s), 8.21 (1H, d). | (Method 5): Rt 4.30 mins, m/z 614 [MH$^+$]. |

Example 28

N-(5-tert-Butyl-3-{3-[(1S,4R)-4-(3-isopropyl-[1,2,4]triazolo[4,3-a]pyridin-6-yloxy)-1,2,3,4-tetrahydro-naphthalen-1-yl]-ureido}-2-methoxy-phenyl)-methanesulfonamide

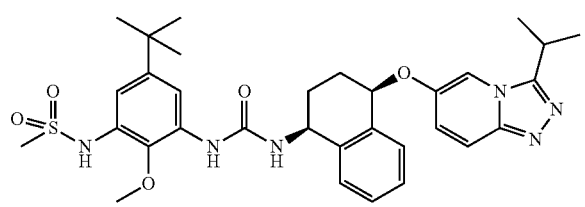 [SMILES: COc1c(NC(=O)N[C@H]2CC[C@@H](Oc3ccc4nnc(C(C)C)n4c3)c3ccccc32)cc(C(C)(C)C)cc1NS(C)(=O)=O]

The title compound was prepared using 5-tert-butyl-3-methanesulfonamido-2-methoxyaniline (for reference procedure see WO2005023761) and Intermediate 1g using analogous procedures to those described in Example 6 step b and Example 1 step h. LCMS (Method 5) Rt 4.30 min, m/z 621.2 [MH+]; $^1$H NMR (400 MHz, CDCl$_3$): 1.28 (9H, s), 1.42-1.45 (3H, d, J 6.9 Hz), 1.45-1.48 (3H, d, J 6.9 Hz), 2.00-2.20 (3H, m), 2.23-2.30 (1H, m), 3.02 (3H, s), 3.20-3.28 (1H, sp, J 6.9 Hz), 3.74 (3H, s), 5.12-5.20 (1H, m), 5.18-5.21 (1H, t, J 4.4 Hz), 5.62-5.66 (1H, d, J 8.8 Hz), 6.88 (1H, s), 6.99-7.03 (1H, dd, J 9.8, 2.0 Hz), 7.06 (1H, s), 7.23-7.35 (4H, m), 7.43-7.45 (1H, d, J 1.8 Hz), 7.47-7.50 (1H, d, J 7.7 Hz), 7.60-7.64 (1H, d, J 9.9 Hz), 7.75-7.77 (1H, d, J 2.3 Hz).

Example 29

1-(3-Fluoro-5-morpholin-4-yl-phenyl)-3-[(1S,4R)-4-(3-isopropyl-[1,2,4]triazolo[4,3-a]pyridin-6-yloxy)-1,2,3,4-tetrahydro-naphthalen-1-yl]-urea

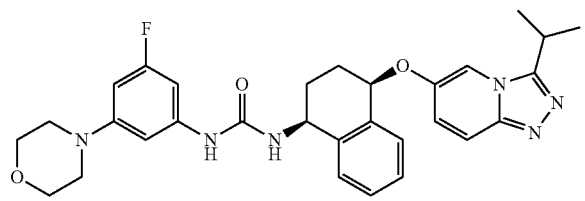 [SMILES: CC(C)c1nnc2ccc(O[C@@H]3CC[C@H](NC(=O)Nc4cc(F)cc(N5CCOCC5)c4)c4ccccc43)cn12]

The title compound was prepared using 3-fluoro-5-(morpholin-4-yl)aniline (Enamine) and Intermediate 1g using analogous procedures to those described in Example 6 step b and Example 1 step h. LCMS (Method 5) Rt 3.98 min, m/z 545.1 [MH+]; $^1$H NMR (400 MHz, CDCl$_3$): 1.41-1.44 (3H, d, J 6.8 Hz), 1.44-1.48 (3H, d, J 6.8 Hz), 2.00-2.20 (3H, m), 2.24-2.32 (1H, m), 3.10-3.14 (4H, t, J 4.7 Hz), 3.20-3.32 (1H, br s), 3.76-3.82 (4H, t, J 4.8 Hz), 5.12-5.24 (2H, m), 6.20-6.28 (2H, d, J 11.7 Hz), 6.58-6.62 (1H, d, J 10.0 Hz), 6.90-6.96 (1H, m), 7.01-7.03 (1H, br s), 7.22-7.34 (3H, m), 7.38-7.46 (1H, br s), 7.50-7.56 (2H, m).

Example 30

1-(3-Fluoro-5-morpholin-4-yl-phenyl)-3-[(1S,4S)-4-(3-isopropyl-[1,2,4]triazolo[4,3-a]pyridin-6-yloxy)-1,2,3,4-tetrahydro-naphthalen-1-yl]-urea

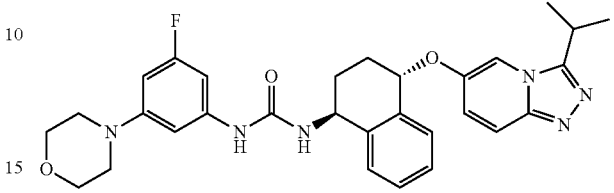

The title compound was prepared using 3-fluoro-5-(morpholin-4-yl)aniline (Enamine) and Intermediate 2c in analogous procedures to that described in Example 6 step b and Example 1 step h. LCMS (Method 5): Rt 3.92 min, m/z 545 [MH+]; $^1$H NMR (400 MHz, d$_6$-DMSO): 1.38 (3H, d), 1.40 (3H, d), 1.80 (1H, m), 2.04 (1H, m), 2.20 (2H, m), 3.07 (4H, dd), 3.58 (1H, sept), 3.71 (4H, dd), 4.97 (1H, m), 5.62 (1H, m), 6.35 (1H, ddd), 6.64 (1H, d), 6.72 (1H, m), 6.81 (1H, ddd), 7.24 (1H, dd), 7.29-7.40 (3H, m), 7.43 (1H, d), 7.69 (1H, d), 8.23 (1H, m), 8.40 (1H, s).

Example 31

1-{5-tert-Butyl-2-(4-fluoro-3-morpholin-4-ylmethyl-phenyl)-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea

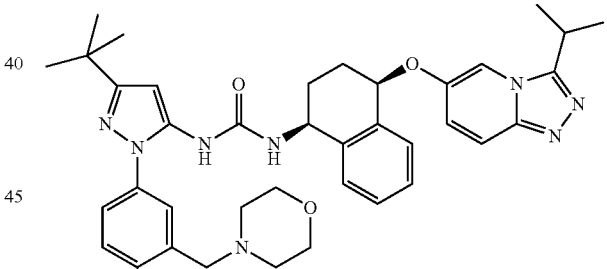

a. 4-(5-Bromo-2-fluoro-benzyl)-morpholine (Intermediate 31a)

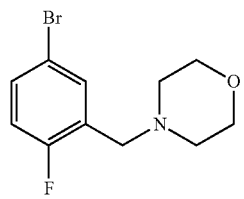 [SMILES: Fc1ccc(Br)cc1CN1CCOCC1]

A solution of 2-bromo-5-fluorobenzaldehyde (2.50 g, 12.30 mmol), morpholine (1.62 g, 18.50 mmol) and acetic acid (0.42 mL), 7.40 mmol) in 1,2-dichloroethane (50 mL) was stirred at RT under nitrogen for 0.5 h. Sodium triacetoxyborohydride (3.92 g, 12.30 mmol) was then added and the mixture stirred for 6 h. Saturated sodium bicarbonate solution (50 mL) was added and the mixture stirred vigorously for 0.5 h. The organic phase was separated and the aqueous phase extracted further with DCM (2×30 mL). The combined organic extracts were washed with water (100 mL) and dried (Na$_2$SO$_4$). The solvent was evaporated and the residue purified by FCC, eluting with 0-50% EtOAc in pentane, to give the title compound as a colourless oil (1.93 g, 57%). LCMS (Method 1): Rt 1.42 min, m/z 274/276 [MH$^+$].

b. Di-tert-butyl 1-[4-fluoro-3-(morpholin-4-ylmethyl)phenyl]hydrazine-1,2-dicarboxylate (Intermediate 31b)

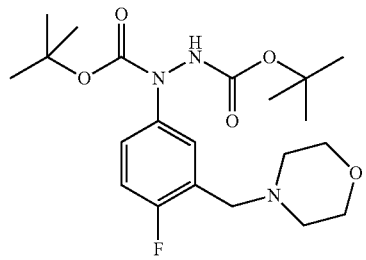 [SMILES: CC(C)(C)OC(=O)NN(C(=O)OC(C)(C)C)c1ccc(F)c(CN2CCOCC2)c1]

n-Butyllithium (1.6 M in hexanes, 5.7 mL, 9.15 mmol) was added dropwise to a stirred solution of Intermediate 31a (1.93 g, 7.04 mmol) in dry THF (15 mL) at −78° C. under nitrogen. The mixture was stirred at −78° C. for 10 min, then di-tert-butyl azodicarboxylate (1.78 g, 7.74 mmol) was added in one portion. The mixture was stirred at −78° C. for 20 min, then allowed to warm to RT over 20 min. The mixture was partitioned between saturated ammonium chloride (15 mL) solution and ethyl acetate (3×20 mL). The combined organic extracts were washed with brine (20 mL) and dried (Na$_2$SO$_4$). The solvent was evaporated and the residue purified by FCC, eluting with 0-100% EtOAc in pentane, to give the title compound as a pale yellow foam (0.71 g, 24%). LCMS (Method 1): Rt 2.35 min, m/z 426 [MH$^+$].

c. 5-tert-Butyl-2-(4-fluoro-3-morpholin-4-ylmethyl-phenyl)-2H-pyrazol-3-ylamine. (Intermediate 31c)

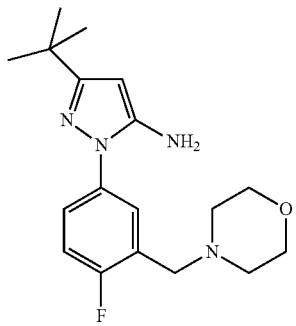 [SMILES: CC(C)(C)c1cc(N)n(-c2ccc(F)c(CN3CCOCC3)c2)n1]

A mixture of Intermediate 31b (0.71 g, 1.67 mmol), pivaloyl acetonitrile (0.21 g, 1.67 mmol) and concentrated HCl (0.84 mL) in ethanol (6 mL) was heated under reflux for 3 h. The cooled mixture was taken to ca. pH 7 with aqueous saturated NaHCO$_3$ and the mixture partitioned between water (10 mL) and EtOAc (3×15 mL). The combined organic extracts were washed with brine (15 mL) and dried (Na$_2$SO$_4$). The solvent was evaporated and the residue triturated (diethyl ether) to give the title compound as a pale yellow solid (239 mg, 43%). LCMS (Method 1): Rt 1.68 min, m/z 333 [MH$^+$].

d. [5-tert-Butyl-2-(4-fluoro-3-morpholin-4-ylmethyl-phenyl)-2H-pyrazol-3-yl]-carbamic acid 2,2,2-trichloro-ethyl ester. (Intermediate 31d)

2,2,2-Trichloroethyl chloroformate (0.097 mL, 0.72 mmol) was added to a solution of Intermediate 31c (239 mg, 0.72 mmol) and DIPEA (0.38 mL, 2.16 mmol) in THF (5 mL) and the mixture stirred for 1 h. The mixture was then partitioned between water (10 mL) and EtOAc (3×15 mL) and the combined organic extracts dried (Na$_2$SO$_4$). The solvent was evaporated to give the title compound as a pale yellow gum (218 mg, 60%). LCMS (Method 1): Rt 2.67 min, m/z 507/509 [MH$^+$]

e. 1-{5-tert-Butyl-2-(4-fluoro-3-morpholin-4-ylmethyl-phenyl)-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea. (Example 31)

The title compound was prepared using Intermediate 31d and Intermediate 1g in an analogous procedure to that described in Example 1 step h. LCMS (Method 5): Rt 3.31 min, m/z 681 [MH$^+$]; $^1$H NMR (300 MHz, CDCl$_3$): 1.33 (9H, s), 1.48 (6H, dd, J 6.8, 12.4 Hz), 1.90-2.03 (1H, m), 2.05-2.16 (2H, m), 2.24-2.31 (1H, m), 2.50 (3H, br s), 3.21-3.31 (1H, m), 3.59 (2H, br s), 3.68 (5H, br s), 5.06-5.13 (1H, m), 5.18-5.21 (1H, m), 5.49 (1H, br s), 6.32 (1H, br s), 6.53 (1H, br s), 7.02-7.07 (1H, m), 7.08-7.16 (1H, m), 7.29 (4H, br s), 7.45 (2H, br s), 7.57-7.64 (2H, m).

Example 32

1-[5-tert-Butyl-2-(3-chloro-4-hydroxy-phenyl)-2H-pyrazol-3-yl]-3-((1S,4R)-4-{3-[2-(2-hydroxy-ethyl-sulfanyl)-phenyl]-[1,2,4]triazolo[4,3-a]pyridin-6-yloxy}-1,2,3,4-tetrahydro-naphthalen-1-yl)-urea

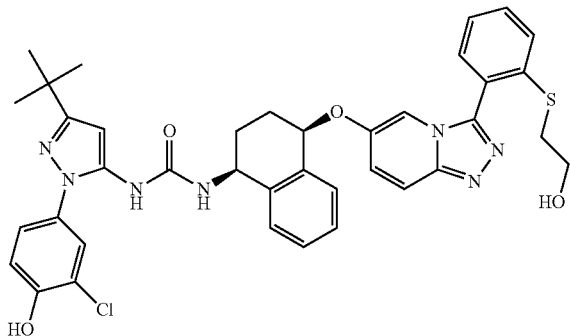 [SMILES: CC(C)(C)c1cc(NC(=O)N[C@H]2CC[C@@H](Oc3ccc4nnc(-c5ccccc5SCCO)n4c3)c3ccccc32)n(-c2ccc(O)c(Cl)c2)n1]

a. [5-tert-Butyl-2-(3-chloro-4-triisopropylsilanyloxy-phenyl)-2H-pyrazol-3-yl]-carbamic acid 2,2,2-trichloro-ethyl ester (Intermediate 32a)

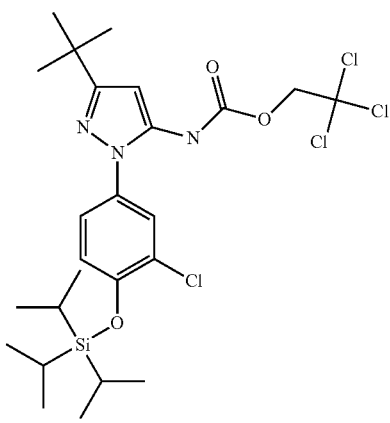 [SMILES: CC(C)[Si](Oc1ccc(-n2nc(C(C)(C)C)cc2NC(=O)OCC(Cl)(Cl)Cl)cc1Cl)(C(C)C)C(C)C]

Trichloroethyl chloroformate (2.76 g, 13.0 mmol) was added dropwise to a solution of 5-tert-butyl-2-(3-chloro-4-triisopropylsilanyloxy-phenyl)-2H-pyrazol-3-ylamine (for reference procedure see WO2009098612; 4.21 g, 10.0 mmol) and diisopropylethylamine (3.87 g, 30.0 mmol) in THF (100 mL). This mixture was stirred for 20 h at RT. The resultant mixture was diluted with ethyl acetate then washed with water, dried (MgSO$_4$) and evaporated in vacuo then purified by FCC, using 0-30% ethyl acetate in cyclohexane, to give the title compound (3.51 g, 5.89 mmol, 58%). LCMS (Method 1): Rt 5.86 min, m/z 596/597 [MH$^+$].

b. 1-[5-tert-Butyl-2-(3-chloro-4-hydroxy-phenyl)-2H-pyrazol-3-yl]-3-((1S,4R)-4-{3-[2-(2-hydroxy-ethylsulfanyl)-phenyl]-[1,2,4]triazolo[4,3-a]pyridin-6-yloxy}-1,2,3,4-tetrahydro-naphthalen-1-yl)-urea (Example 32)

Intermediate 10d (25 mg, 0.043 mmol), Intermediate 32a (51 mg, 0.085 mmol) and diisopropylethylamine (22 mg, 0.171 mmol) were dissolved in DMF (2.0 mL) and stirred for 30 min at 60° C. After cooling, the mixture was purified using an SCX-2 cartridge, washing with MeOH and eluting with 2M NH$_3$ in MeOH, to give a residue. This was dissolved in THF (1.0 mL) and triethylamine-trihydrogen-fluoride (4 drops) was added. This mixture was left at RT for 20 h and then diluted with saturated sodium hydrogen carbonate solution (10 mL) and extracted with ethyl acetate (3×). The combined organic extracts were evaporated in vacuo. Purification by HPLC (C18 X-select column, 35-55% MeCN in H$_2$O, 0.1% formic acid) gave the title compound (5.0 mg, 16%). LCMS (Method 5): Rt 4.43 min, m/z 724.2 [MH$^+$]. $^1$H NMR (400 MHz, d$_4$-MeOD): 1.32 (9H, s), 1.86-2.11 (4H, m), 2.21-2.30 (1H, m), 2.97-3.03 (2H, dt, J 6.6, 2.6 Hz), 3.61 (2H, t, J 6.63 Hz), 4.75 (1H, br s), 5.35 (1H, t, J 3.88 Hz), 6.31 (1H, s), 6.99 (1H, d, J 8.26 Hz), 7.18-7.25 (3H, m), 7.26-7.34 (2H, m), 7.37 (1H, dd, J 10.26, 2.13 Hz), 7.41 (1H, d, J 2.63 Hz), 7.46 (1H, dt, J 7.63, 1.0 Hz), 7.53-7.58 (2H, m), 7.63 (1H, dt, J 7.5, 1.8 Hz), 7.72 (1H, d, J 8.26 Hz), 7.78 (1H, dd, J 10.1, 0.88 Hz), 8.55 (1H, s).

Example 33

1-[5-tert-Butyl-2-(3-chloro-4-hydroxy-phenyl)-2H-pyrazol-3-yl]-3-((1S,4S)-4-{3-[2-(2-hydroxy-ethyl-sulfanyl)-phenyl]-[1,2,4]triazolo[4,3-a]pyridin-6-yloxy}-1,2,3,4-tetrahydro-naphthalen-1-yl)-urea

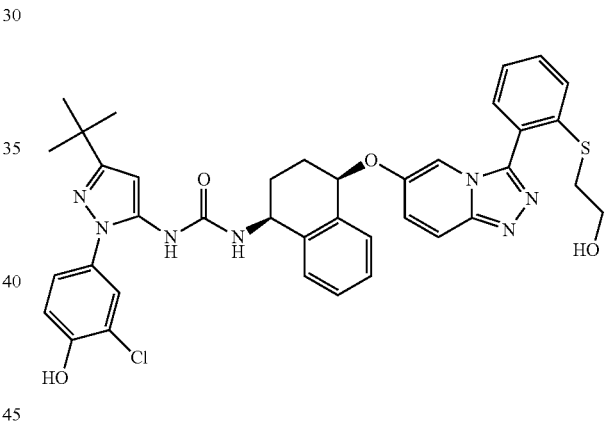

(1S,4S)-4-{3-[2-(2-Triisopropylsilanyloxy-ethylsulfanyl)-phenyl]-[1,2,4]triazolo[4,3-a]pyridin-6-yloxy}-1,2,3,4-tetrahydro-naphthalen-1-ylamine (Prepared using analogous procedures to those described in Example 10 step d: 25 mg, 0.043 mmol), Intermediate 32a (51 mg, 0.085 mmol) and diisopropylethylamine (22 mg, 0.171 mmol) were dissolved in DMF (2.0 mL) and stirred at 60° C. for 30 min. After cooling, the mixture was purified using a SCX-2 cartridge, washing with MeOH and eluting with 2M NH$_3$ in MeOH, to give a residue. This was dissolved in THF (1.0 mL) and triethylamine-trihydrogenfluoride (4 drops) was added. This mixture was left at RT for 20 h and the mixture was diluted with saturated sodium hydrogen carbonate solution (10 mL) and extracted with ethyl acetate (3×). The combined organic extracts were evaporated in vacuo then further purified by HPLC (C18 X-select column, 35-55% MeCN in H$_2$O, 0.1% formic acid) to give the title compound (2.0 mg, 6.5%). LCMS (Method 5): Rt 4.43 min, m/z 724.2 [MH$^+$]. $^1$H NMR (400 MHz, d$_4$-MeOD): 1.31 (9H, s), 1.71-1.80 (1H, m), 2.10-2.20 (4H, m), 2.99 (2H, dt, J 6.7, 1.7 Hz), 3.60 (2H, t, J 6.5 Hz), 4.51 (1H, br s), 4.97 (1H, t, J 5.5 Hz), 5.41 (1H, t, J 4.9 Hz), 6.29 (1H, s), 6.90 (1H, d, J 8.2 Hz), 7.16-7.25

(3H, m), 7.27-7.31 (2H, m), 7.36-7.41 (2H, m), 7.43-7.48 (1H, m), 7.53 (1H, dd, J 7.7, 1.5 Hz), 7.63 (1H, dt, J 7.5, 1.2 Hz), 7.72 (1H, dd, J 8.1, 0.7 Hz), 7.77 (1H, d, J 10.0 Hz), 8.55 (1H, s).

Example 34

1-(5-tert-Butyl-2-p-tolyl-2H-pyrazol-3-yl)-3-{(1S, 4R)-4-[3-(2-pyrrolidin-1-yl-pyridin-4-yl)-[1,2,4] triazolo[4,3-a]pyridin-6-yloxy]-1,2,3,4-tetrahydro-naphthalen-1-yl}-urea, formate salt

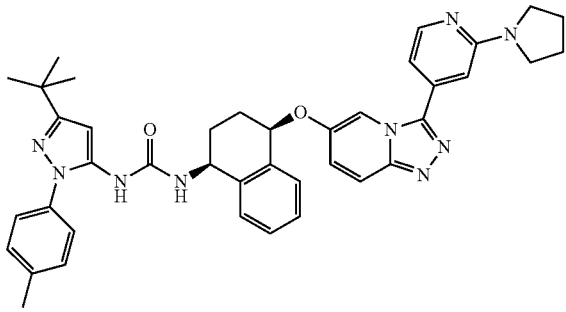 [SMILES: Cc1ccc(-n2nc(C(C)(C)C)cc2NC(=O)N[C@H]2CC[C@@H](Oc3ccc4nnc(-c5ccnc(N6CCCC6)c5)n4c3)c3ccccc32)cc1]

a. 6-Fluoro-[1,2,4]triazolo[4,3-a]pyridine (Intermediate 34a)

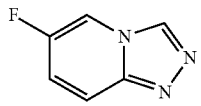

5-Fluoro-2-hydrazinyl-pyridine (for reference procedure see WO2010022076; 1.00 g, 7.87 mmol) was dissolved in diethoxymethylacetate (10 mL) and stirred for 90 min. The resultant solid was filtered, washed with cyclohexane and dried in vacuo to give the title compound (904 mg, 84%). $^1$H NMR (400 MHz, CDCl$_3$): 7.21-7.29 (1H, ddd, J 9.8, 7.7, 2.3 Hz), 7.80-7.87 (1H, dd, J 9.9, 4.8 Hz), 8.07-8.09 (1H, m), 8.84 (1H, s).

b. 3-Bromo-6-fluoro-[1,2,4]triazolo[4,3-a]pyridine (Intermediate 34b)

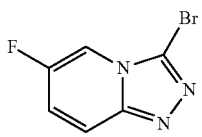

Intermediate 34a (908 mg, 6.60 mmol) was dissolved in DCM (50 mL) and N-bromosuccinimide (1.29 g, 7.26 mmol) added. The reaction was heated to 45° C. for 4 h, then cooled and partitioned between DCM (150 mL) and saturated aqueous NaHCO$_3$ (150 mL), and extracted into DCM (3×). The combined organic layers were washed with brine, dried (MgSO$_4$) and evaporated in vacuo. Purification by FCC, using 0-5% [2M NH$_3$ in MeOH] in DCM, gave the title compound (900 mg, 63%). LCMS (Method 1): Rt 1.94 min, m/z 216/218 [MH$^+$].

c. 6-Fluoro-3-(2-pyrrolidin-1-yl-pyridin-4-yl)-[1,2,4] triazolo[4,3-a]pyridine (Intermediate 34c)

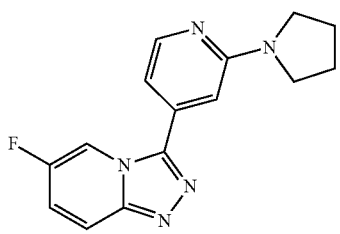 [SMILES: Fc1ccc2nnc(-c3ccnc(N4CCCC4)c3)n2c1]

Degassed (sparged with argon for 10 min) dioxane/water (2:1, 9.0 mL) was added to Intermediate 34b (200 mg, 0.93 mmol), 5-(pyrrolidino)pyridine-3-boronic acid pinacol ester (304 mg, 1.11 mmol), sodium carbonate (296 mg, 2.79 mmol) and tetrakistriphenylphosphine palladium (54.0 mg, 0.046 mmol). The reaction was heated to 85° C. for 5 h and then cooled. The mixture was partitioned between EtOAc (50 mL) and water (50 mL), and extracted into EtOAc (3×). The combined organic layers were washed with brine, dried (MgSO$_4$) and evaporated in vacuo. Purification by FCC, using 0-10% MeOH in DCM, gave the title compound (200 mg, 0.71 mmol, 76%). LCMS (Method 1): Rt 0.34 min, 1.72 min, m/z 284 [MH$^+$].

d. (1S,4R)-4-[3-(2-Pyrrolidin-1-yl-pyridin-4-yl)-[1, 2,4]triazolo[4,3-a]pyridin-6-yloxy]-1,2,3,4-tetra-hydro-naphthalen-1-ylamine (Intermediate 34d)

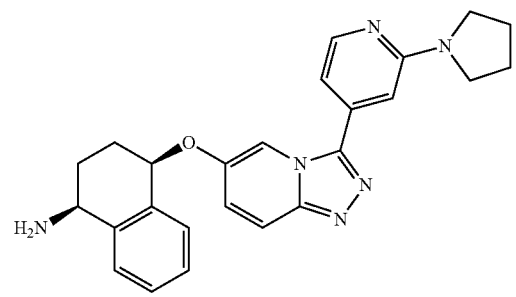 [SMILES: N[C@H]1CC[C@@H](Oc2ccc3nnc(-c4ccnc(N5CCCC5)c4)n3c2)c2ccccc21]

Intermediate 1d (115 mg, 0.71 mmol) was added to a suspension of sodium hydride (60% in mineral oil, 85.0 mg, 2.12 mmol) in DMF (2 mL). The reaction was stirred for 20 min, then Intermediate 34c (200 mg, 0.71 mmol) in DMF (2 mL) was added and the reaction heated to 60° C. for 2 h. After cooling, the reaction was quenched by dropwise addition of MeOH. The solution was diluted with MeOH and loaded onto an SCX-2 cartridge, which was washed sequentially with MeOH and 2M NH$_3$ in MeOH. The basic fractions were evaporated in vacuo then purified by FCC, using 0-10% [2M NH$_3$ in MeOH] in DCM, to give the title compound, contaminated with several impurities (70 mg). The reaction was progressed to the next step without further purification.

e. 1-(5-tert-Butyl-2-p-tolyl-2H-pyrazol-3-yl)-3-{(1S,4R)-4-[3-(2-pyrrolidin-1-yl-pyridin-4-yl)-[1,2,4]triazolo[4,3-a]pyridin-6-yloxy]-1,2,3,4-tetrahydro-naphthalen-1-yl}-urea formate salt (Example 34)

To Intermediate 34d (70 mg) dissolved in 1,4-dioxane (2 mL), (5-tert-butyl-2-p-tolyl-2H-pyrazol-3-yl)-carbamic acid 2,2,2-trichloro-ethyl ester (Synthetic Communications, 39(22), 3999-4009; 2009; 62.0 mg, 0.15 mmol) and DIPEA (56.0 µL, 0.30 mmol) were added. The resulting reaction was heated to 60° C. for 18 h. After cooling, the mixture was partitioned between EtOAc (50 mL) and water (50 mL), and extracted into EtOAc (3×). The combined organic layers were washed with brine, dried (MgSO$_4$) and evaporated in vacuo. The residue was purified by FCC, using 0-10% [2M NH$_3$ in MeOH] in DCM, then further purified by HPLC (C18 X-select column, 10-60% MeCN in H$_2$O, 0.1% formic acid) to give the title compound as a partially in the form of formic acid salt (15.0 mg, 0.022 mmol, 3%). LCMS (Method 5) Rt 4.18 min, m/z 682 [MH$^+$]. $^1$H NMR (400 MHz, d$_4$-MeOD): 1.29 (9H, s), 1.90-2.10 (7H, m), 2.20-2.30 (1H, m), 2.38 (3H, s), 3.47-3.55 (4H, m), 4.84-4.90 (1H, dd, J 6.0, 8.8), 5.36-5.40 (1H, t, J 4.1), 6.32 (1H, s), 6.64-6.68 (1H, d, J 9.0), 7.19-7.34 (11H, m), 7.67-7.71 (1H, d, J 10.0), 7.84-7.88 (1H, dd, J 9.0, 2.3), 7.90-7.92 (1H, d, J 1.7), 8.42-8.44 (1H, d, J 2.3), 8.50 (0.7H, br s, formate).

Biological Assays

P38alpha Enzyme Inhibition Assay

The inhibitory activity of compounds was determined using an Alphascreen® (Perkin Elmer) based kinase activity assay. Kinase reactions consisted of 25 mM HEPES pH 7.5, 10 mM MgCl$_2$, 100 µM Na$_3$VO$_4$, 2 mM DTT, 0.05 mg/ml Tween 20, 100 pM p38alpha (Invitrogen, PV3304), 1% DMSO and 0.3 µg/ml ATF-2 fusion protein (New England Biolabs, 9224). Compounds were incubated under these conditions for 2 hours, at 25° C., prior to the initiation of the kinase activity by the addition of the 250 µM ATP. Reaction volumes were 20 uL. After 1 hr at 25° C. reactions were stopped by the adding 10 uL of 25 mM HEPES pH 7.5 containing 62.5 mM EDTA, 0.05% Triton X-100, 10% BSA and 0.83 ng/uL anti-phospho-ATF2 antibody (Abcam, ab28812). Detection was performed by measuring luminescence following the addition of Alphascreen Donor beads (Perkin Elmer 6765300) and Protein A Alphascreen Acceptor beads (Perkin Elmer 6760137), both at a final concentration of 20 ug/ml. IC$_{50}$ values were determined from concentration-response curves.

Results are shown in the following Table:

| Example | p38α inhibition |
| --- | --- |
| 1 | ++++ |
| 2 | ++++ |
| 3 | ++++ |
| 4 | ++++ |
| 5 | ++++ |
| 6 | ++++ |
| 7 | ++++ |
| 8 | ++++ |
| 9 | ++++ |
| 10 | ++++ |
| 11 | ++++ |
| 12 | ++++ |
| 13 | +++ |
| 14 | ++++ |
| 15 | ++++ |
| 16 | ++++ |
| 17 | ++++ |
| 18 | ++++ |
| 19 | ++++ |
| 20 | ++++ |
| 21 | ++++ |
| 22 | ++++ |
| 23 | ++++ |
| 24 | ++++ |
| 25 | ++++ |
| 26 | ++++ |
| 27 | ++++ |
| 28 | ++++ |
| 29 | ++++ |
| 30 | ++++ |
| 31 | ++++ |

In the table above, p38α binding potencies (IC$_{50}$ values) are indicated as follows: 7000-500 nM '+'; 500-100 nM '++'; 100-10 nM '+++'; <10 nM '++++'.

The invention claimed is:

1. A compound selected from the group consisting of:
 1-(5-tert-Butyl-2-phenyl-2H-pyrazol-3-yl)-3-[4-(3-isopropyl-[1,2,4]triazolo[4,3-a]pyridin-6-yloxy)-1,2,3,4-tetrahydro-naphthalen-1-yl]-urea;
 1-Cyclopropyl-3-[4-(3-isopropyl-[1,2,4]triazolo[4,3-a]pyridin-6-yloxy)-1,2,3,4-tetrahydro-naphthalen-1-yl]-urea;
 1-(5-tert-Butyl-2-p-tolyl-2H-pyrazol-3-yl)-3-[3-(3-isopropyl-[1,2,4]triazolo[4,3-a]pyridin-6-ylsulfanyl)-indan-1-yl]-urea;
 1-(5-tert-Butyl-2-p-tolyl-2H-pyrazol-3-yl)-3-[4-{3-[3-(2-morpholin-4-yl-ethoxy)-phenyl]-[1,2,4]triazolo[4,3-a]pyridin-6-yloxy}-1,2,3,4-tetrahydro-naphthalen-1-yl)-urea;
 1-(5-tert-Butyl-2-p-tolyl-2H-pyrazol-3-yl)-3-[4-(3-isopropyl-[1,2,4]triazolo[4,3-a]pyridin-7-yloxy)-1,2,3,4-tetrahydro-naphthalen-1-yl]-urea;
 1-{5-tert-Butyl-2-[3-(2-morpholin-4-yl-ethoxy)-phenyl]-2H-pyrazol-3-yl}-3-[4-(3-isopropyl-[1,2,4]triazolo[4,3-a]pyridin-6-yloxy)-1,2,3,4-tetrahydro-naphthalen-1-yl]-urea;
 1-(5-tert-Butyl-isoxazol-3-yl)-3-[3-(3-isopropyl-[1,2,4]triazolo[4,3-a]pyridin-6-yloxy)-indan-1-yl]-urea;
 1-{5-tert-Butyl-2-[3-(2-dimethylamino-ethoxy)-phenyl]-2H-pyrazol-3-yl}-3-[4-(3-isopropyl-[1,2,4]triazolo[4,3-a]pyridin-6-yloxy)-1,2,3,4-tetrahydro-naphthalen-1-yl]-urea;
 1-[5-tert-Butyl-2-(4-hydroxy-phenyl)-2H-pyrazol-3-yl]-3-[4-(3-isopropyl-[1,2,4]triazolo[4,3-a]pyridin-6-yloxy)-1,2,3,4-tetrahydro-naphthalen-1-yl]-urea;
 1-(5-tert-Butyl-2-p-tolyl-2H-pyrazol-3-yl)-3-[4-(3-cyclopentyl-[1,2,4]triazolo[4,3-a]pyridin-6-yloxy)-1,2,3,4-tetrahydro-naphthalen-1-yl]-urea;
 1-[5-tert-Butyl-2-(3-morpholin-4-ylmethyl-phenyl)-2H-pyrazol-3-yl]-3-[4-(3-isopropyl-[1,2,4]triazolo[4,3-a]pyridin-6-yloxy)-1,2,3,4-tetrahydro-naphthalen-1-yl]-urea;
 1-(5-tert-Butyl-2-p-tolyl-2H-pyrazol-3-yl)-3-[4-(3-cyclopropyl-[1,2,4]triazolo[4,3-a]pyridin-6-yloxy)-1,2,3,4-tetrahydro-naphthalen-1-yl}-urea;
 1-(5-tert-Butyl-2-p-tolyl-2H-pyrazol-3-yl)-3-[4-(3-pyridin-2-yl-[1,2,4]triazolo[4,3-a]pyridin-6-yloxy)-1,2,3,4-tetrahydro-naphthalen-1-yl}-urea;
 1-[5-tert-Butyl-2-(3-chloro-4-hydroxy-phenyl)-2H-pyrazol-3-yl]-3-[4-(3-isopropyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[4-(3-cyclohexyl-[1,2,4]triazolo[4,3-a]pyridin-6-yloxy)-1,2,3,4-tetrahydro-naphthalen-1-yl]-urea;

1-[5-tert-Butyl-2-(4-chloro-3-hydroxy-phenyl)-2H-pyrazol-3-yl]-3-[4-(3-isopropyl-[1,2,4]triazolo[4,3-a]pyridin-6-yloxy)-1,2,3,4-tetrahydro-naphthalen-1-yl]-urea;

1-(3-Fluoro-5-morpholin-4-yl-phenyl)-3-[4-(3-isopropyl-[1,2,4]triazolo[4,3-a]pyridin-6-yloxy)-1,2,3,4-tetrahydro-naphthalen-1-yl]-urea;

1-{5-tert-Butyl-2-(4-fluoro-3-morpholin-4-ylmethyl-phenyl)-2H-pyrazol-3-yl}-3-[4-(3-isopropyl-[1,2,4]triazolo[4,3-a]pyridin-6-yloxy)-1,2,3,4-tetrahydro-naphthalen-1-yl]-urea;

1-[5-tert-Butyl-2-(3-chloro-4-hydroxy-phenyl)-2H-pyrazol-3-yl]-3-(4-{3-[2-(2-hydroxy-ethylsulfanyl)-phenyl]-[1,2,4]triazolo[4,3-a]pyridin-6-yloxy}-1,2,3,4-tetrahydro-naphthalen-1-yl)-urea;

1-[5-tert-Butyl-2-(3-chloro-4-hydroxy-phenyl)-2H-pyrazol-3-yl]-3-(4-{3-[2-(2-hydroxy-ethylsulfanyl)-phenyl]-[1,2,4]triazolo[4,3-a]pyridin-6-yloxy}-1,2,3,4-tetrahydro-naphthalen-1-yl)-urea; and 1-(5-tert-Butyl-2-p-tolyl-2H-pyrazol-3-yl)-3-{4-[3-(2-pyrrolidin-1-yl-pyridin-4-yl)-[1,2,4]triazolo[4,3-a]pyridin-6-yloxy]-1,2,3,4-tetrahydro-naphthalen-1-yl}-urea, or a pharmaceutically acceptable salt of said compound.

2. A compound, which is selected from the group consisting of:

1-Cyclopropyl-3-[(1S,4S)-4-(3-isopropyl-[1,2,4]triazolo[4,3-a]pyridin-6-yloxy)-1,2,3,4-tetrahydro-naphthalen-1-yl]-urea;

(±)-trans-1-(5-tert-Butyl-2-p-tolyl-2H-pyrazol-3-yl)-3-[3-(3-isopropyl-[1,2,4]triazolo[4,3-a]pyridin-6-ylsulfanyl)-indan-1-yl]-urea;

1-(5-tert-Butyl-2-p-tolyl-2H-pyrazol-3-yl)-3-[(1S,4R)-4-{3-[3-(2-morpholin-4-yl-ethoxy)-phenyl]-[1,2,4]triazolo[4,3-a]pyridin-6-yloxy}-1,2,3,4-tetrahydro-naphthalen-1-yl)-urea;

1-(5-tert-Butyl-2-p-tolyl-2H-pyrazol-3-yl)-3-[(1S,4R)-4-(3-isopropyl-[1,2,4]triazolo[4,3-a]pyridin-7-yloxy)-1,2,3,4-tetrahydro-naphthalen-1-yl]-urea;

1-{5-tert-Butyl-2-[3-(2-morpholin-4-yl-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-{(1S,4R)-4-(3-(2-hydroxy-phenyl)-[1,2,4]triazolo[4,3-a]pyridin-6-yloxy)-1,2,3,4-tetrahydro-naphthalen-1-yl}-urea;

1-(5-tert-Butyl-isoxazol-3-yl)-3-[(1S,3S)-3-(3-isopropyl-[1,2,4]triazolo[4,3-a]pyridin-6-yloxy)-indan-1-yl]-urea;

1-(5-tert-Butyl-2-p-tolyl-2H-pyrazol-3-yl)-3-{(1S,4R)-4-[3-(2-hydroxy-ethylsulfanyl)-phenyl]-[1,2,4]triazolo[4,3-a]pyridin-6-yloxy)-1,2,3,4-tetrahydro-naphthalen-1-yl-urea;

1-{5-tert-Butyl-2-[3-(2-dimethylamino-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(3-chloro-4-hydroxy-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea;

1-Cyclopropyl-3-[(1S,4R)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(4-chloro-3-hydroxyphenyl)-2H-pyrazol-3-yl]-3-[(1S,4R)-4-(3-isopropyl-[1,2,4]triazolo[4,3-a]pyridin-6-yloxy)-1,2,3,4-tetrahydronaphthalen-1-yl]-urea;

1-[5-tert-Butyl-2-(4-hydroxy-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea;

1-(5-tert-Butyl-isoxazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[(1S,4R)-4-(3-cyclopentyl-[1,2,4]triazolo[4,3-a]pyridin-6-yloxy)-1,2,3,4-tetrahydro-naphthalen-1-yl]-urea;

1-[5-tert-Butyl-2-(3-morpholin-4-ylmethyl-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl-3-{(1S,4R)-4-(3-(2,6-dichloro-phenyl)-[1,2,4]triazolo[4,3-a]pyridin-6-yloxy)-1,2,3,4-tetrahydro-naphthalen-1-yl}-urea;

1-(5-tert-Butyl-2-p-tolyl-2H-pyrazol-3-yl-3-yl)-3-[(1S,4R)-4-(3-cyclopropyl-[1,2,4]triazolo[4,3-a]pyridin-6-yloxy)-1,2,3,4-tetrahydro-naphthalen-1-yl}-urea;

1-(5-tert-Butyl-2-p-tolyl-2H-pyrazol-3-yl-3-yl)-3-[(1S,4R)-4-(3-pyridin-2-yl-[1,2,4]triazolo[4,3-a]pyridin-6-yloxy)-1,2,3,4-tetrahydro-naphthalen-1-yl}-urea;

1-(5-tert-Butyl-2-p-tolyl-2H-pyrazol-3-yl-3-{(1S,4R)-4-(3-(2-chloro-phenyl)-[1,2,4]triazolo[4,3-a]pyridin-6-yloxy)-1,2,3,4-tetrahydro-naphthalen-1-yl}-urea;

1-{(1S,4R)-4-[3-(2-Benzyloxy-phenyl)-[1,2,4]triazolo[4,3-a]pyridin-6-yloxy)-1,2,3,4-tetrahydro-naphthalen-1-yl}-3-(5-tert-butyl-2-p-tolyl-2H-pyrazol-3-yl)-urea;

1-[5-tert-Butyl-2-(3-chloro-4-hydroxy-phenyl)-2H-pyrazol-3-yl]-3-[(1S,4S)-4-(3-isopropyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[(1S,4R)-4-(3-cyclohexyl-[1,2,4]triazolo[4,3-a]pyridin-6-yloxy)-1,2,3,4-tetrahydro-naphthalen-1-yl]-urea;

1-[5-tert-Butyl-2-(4-chloro-3-hydroxy-phenyl)-2H-pyrazol-3-yl]-3-[(1S,4S)-4-(3-isopropyl-[1,2,4]triazolo[4,3-a]pyridin-6-yloxy)-1,2,3,4-tetrahydro-naphthalen-1-yl]-urea;

1-(3-Fluoro-5-morpholin-4-yl-phenyl)-3-[(1S,4R)-4-(3-isopropyl-[1,2,4]triazolo[4,3-a]pyridin-6-yloxy)-1,2,3,4-tetrahydro-naphthalen-1-yl]-urea;

1-(3-Fluoro-5-morpholin-4-yl-phenyl)-3-[(1S,4S)-4-(3-isopropyl-[1,2,4]triazolo[4,3-a]pyridin-6-yloxy)-1,2,3,4-tetrahydro-naphthalen-1-yl]-urea;

1-{5-tert-Butyl-2-(4-fluoro-3-morpholin-4-ylmethyl-phenyl)-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(3-chloro-4-hydroxy-phenyl)-2H-pyrazol-3-yl]-3-((1S,4R)-4-{3-[2-(2-hydroxy-ethylsulfanyl)-phenyl]-[1,2,4]triazolo[4,3-a]pyridin-6-yloxy}-1,2,3,4-tetrahydro-naphthalen-1-yl)-urea;

1-[5-tert-Butyl-2-(3-chloro-4-hydroxy-phenyl)-2H-pyrazol-3-yl]-3-((1S,4S)-4-{3-[2-(2-hydroxy-ethylsulfanyl)-phenyl]-[1,2,4]triazolo[4,3-a]pyridin-6-yloxy}-1,2,3,4-tetrahydro-naphthalen-1-yl)-urea;

1-(5-tert-Butyl-2-p-tolyl-2H-pyrazol-3-yl)-3-{(1S,4R)-4-[3-(2-pyrrolidin-1-yl-pyridin-4-yl)-[1,2,4]triazolo[4,3-a]pyridin-6-yloxy]-1,2,3,4-tetrahydro-naphthalen-1-yl}-urea; and N-(4-{(1R,4S)-4-[3-(5-tert-Butyl-2-p-tolyl-2H-pyrazol-3-yl)-ureido]-1,2,3,4-tetrahydro-naphthalen-1-yloxymethyl}-pyridin-2-yl)-2-methoxy-acetamide;

1-(5-tert-Butyl-2-p-tolyl-2H-pyrazol-3-yl)-3-[(1S,4R)-4-(3-tert-butyl-[1,2,4]triazolo[4,3-a]pyridin-6-yloxy)-1,2,3,4-tetrahydro-naphthalen-1-yl]-urea; and N-(5-tert-Butyl-3-{3-[(1S,4R)-4-(3-isopropyl-[1,2,4]triazolo[4,3-a]pyridin-6-yloxy)-1,2,3,4-tetrahydro-naphthalen-1-yl]-ureido}-2-methoxy-phenyl)-methanesulfonamide, or a pharmaceutically acceptable salt of said compound.

3. A compound represented by formula (Ia):

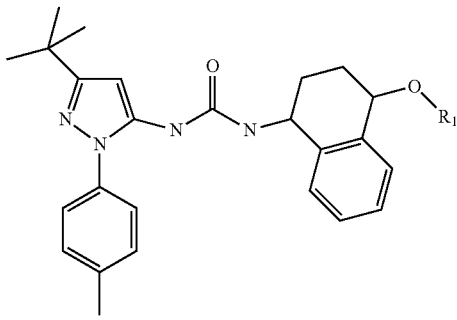

(Ia)

wherein $R^1$ represents a member selected from the group consisting of:

3-[3-(2-morpholin-4-yl-ethoxy)-phenyl]-[1,2,4]triazolo[4,3-a]pyridin-6-yl;
(3-isopropyl-[1,2,4]triazolo[4,3-a]pyridin-7-yl;
{2-[(methoxyacetyl)amino]pyridin-4-yl}methyl;
3-cyclopentyl-[1,2,4]triazolo[4,3-a]pyridin-6-yl;
3-cyclopropyl-[1,2,4]triazolo[4,3-a]pyridin-6-yl;
3-pyridin-2-yl-[1,2,4]triazolo[4,3-a]pyridin-6-yl;
3-cyclohexyl-[1,2,4]triazolo[4,3-a]pyridin-6-yl; and
3-(2-pyrrolidin-1-yl-pyridin-4-yl)-[1,2,4]triazolo[4,3-a]pyridin-6-yl;

or a pharmaceutically acceptable salt of said compound.

4. A compound represented by formula (Ib)

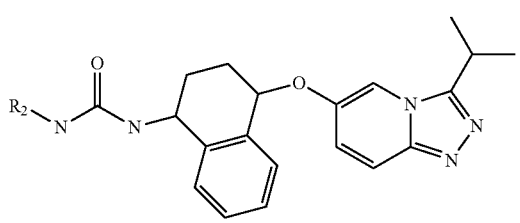

(Ib)

wherein $R^2$ represents a member selected from the group consisting of:

5-tert-Butyl-2-phenyl-2H-pyrazol-3-yl;
Cyclopropyl;
5-tert-Butyl-2-[3-(2-morpholin-4-yl-ethoxy)-phenyl]-2H-pyrazol-3-yl;
5-tert-Butyl-2-[3-(2-dimethylamino-ethoxy)-phenyl]-2H-pyrazol-3-yl;
5-tert-Butyl-2-(3-chloro-4-hydroxy-phenyl)-2H-pyrazol-3-yl;
5-tert-Butyl-2-(4-chloro-3-hydroxyphenyl)-2H-pyrazol-3-yl;
5-tert-Butyl-2-(4-hydroxy-phenyl)-2H-pyrazol-3-yl;
5-tert-Butyl-2-(3-morpholin-4-ylmethyl-phenyl)-2H-pyrazol-3-yl;
5-tert-Butyl-3-methanesulfonylamino-2-methoxy-phenyl;
3-Fluoro-5-morpholin-4-yl-phenyl; and
5-tert-Butyl-2-(4-fluoro-3-morpholin-4-ylmethyl-phenyl)-2H-pyrazol-3-yl;

or a pharmaceutically acceptable salt of said compound.

5. A pharmaceutical composition, comprising a compound as claimed in claim 1 and at least one pharmaceutically acceptable carrier.

6. A composition as claimed in claim 5 which is adapted for inhalation for pulmonary administration.

7. A method of treating a disease or condition in a human subject, comprising administering to the subject an effective amount of a compound of claim 1, wherein the disease or condition is chronic eosinophilic pneumonia, asthma, COPD, adult respiratory distress syndrome (ARDS), exacerbation of airways hyper-reactivity consequent to other drug therapy or airways disease that is associated with pulmonary hypertension.

8. A pharmaceutical composition, comprising a compound as claimed in claim 3 and at least one pharmaceutically acceptable carrier.

9. A composition as claimed in claim 8, which is adapted for inhalation for pulmonary administration.

10. A method of treating a disease or condition in a human subject, comprising administering to the subject an effective amount of a compound of claim 3, wherein the disease or condition is chronic eosinophilic pneumonia, asthma, COPD, adult respiratory distress syndrome (ARDS), exacerbation of airways hyper-reactivity consequent to other drug therapy or airways disease that is associated with pulmonary hypertension.

11. A pharmaceutical composition, comprising a compound as claimed in claim 4 and at least one pharmaceutically acceptable carrier.

12. A composition as claimed in claim 11, which is adapted for inhalation for pulmonary administration.

13. A method of treating a disease or condition in a human subject, comprising administering to the subject an effective amount of a compound of claim 4, wherein the disease or condition is chronic eosinophilic pneumonia, asthma, COPD, adult respiratory distress syndrome (ARDS), exacerbation of airways hyper-reactivity consequent to other drug therapy or airways disease that is associated with pulmonary hypertension.

* * * * *